US008859750B2

(12) United States Patent
Meyers et al.

(10) Patent No.: US 8,859,750 B2
(45) Date of Patent: Oct. 14, 2014

(54) RNAI MODULATION OF RSV AND THERAPEUTIC USES THEREOF

(75) Inventors: Rachel Meyers, Newton, MA (US); Muthiah Manoharan, Weston, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/434,820

(22) Filed: Mar. 29, 2012

(65) Prior Publication Data
US 2013/0005791 A1    Jan. 3, 2013

Related U.S. Application Data

(63) Continuation of application No. 12/021,245, filed on Jan. 28, 2008, now Pat. No. 8,158,773, which is a continuation-in-part of application No. 11/411,291, filed on Apr. 26, 2006, now Pat. No. 7,517,865, which is a continuation-in-part of application No. 11/326,956, filed on Jan. 6, 2006, now Pat. No. 7,507,809.

(60) Provisional application No. 60/642,364, filed on Jan. 7, 2005, provisional application No. 60/659,828, filed on Mar. 9, 2005.

(51) Int. Cl.
C07H 21/04     (2006.01)
C12N 15/113    (2010.01)

(52) U.S. Cl.
CPC ........ *C12N 15/1131* (2013.01); *C12N 2310/14* (2013.01); *C12N 2320/31* (2013.01)
USPC .......................................... 536/24.5; 514/44

(58) Field of Classification Search
CPC combination set(s) only.
See application file for complete search history.

(56) References Cited

U.S. PATENT DOCUMENTS

| | | | |
|---|---|---|---|
| 7,427,605 B2 | 9/2008 | Davis et al. | |
| 7,718,629 B2 | 5/2010 | Bumcrot et al. | |
| 2003/0143732 A1 | 7/2003 | Fosnaugh et al. | |
| 2003/0170891 A1 | 9/2003 | McSwiggen | |
| 2004/0259247 A1 | 12/2004 | Tuschl et al. | |
| 2006/0263435 A1 | 11/2006 | Davis et al. | |
| 2007/0004664 A1 | 1/2007 | McSwiggen et al. | |
| 2007/0031844 A1 | 2/2007 | Khvorova et al. | |
| 2007/0281899 A1 | 12/2007 | Bumcrot et al. | |
| 2009/0149403 A1 | 6/2009 | MacLachlan | |
| 2011/0015250 A1 | 1/2011 | Bumcrot et al. | |

FOREIGN PATENT DOCUMENTS

| | | |
|---|---|---|
| WO | WO 2004/080406 | 9/2004 |
| WO | WO 2004/090108 | 10/2004 |

OTHER PUBLICATIONS

Agrawal, S., et al., "Antisense oligonucleotides: towards clinical trials." Trends in Biotechnology. Oct. 1996, vol. 14, pp. 376-387.
Bass, B., "The short answer," Nature, May 24, 2001, pp. 428-429, vol. 411.
Elbashir, S., et al., "Analysis of gene function in somatic mammalian cells using small interfering RNAs," Methods, 2002, pp. 199-213, vol. 26.
Elbashir, S., et al., "Duplexes of 21-nucleotide RNAs mediate RNA interference in mammalian cell culture," Nature, May 24, 2001, p. 494-498, vol. 411.
Elbashir, S., et al., "Functional Anatomy of siRNAs for Mediating Efficient RNAi in *Drosophila melanogaster* Embryo Lysate", The EMBO Journal, 2001, pp. 6877-6888, vol. 20, No. 23.
Elbashir, S., et al., "RNA Interference is Mediated by 21-and 22 Nucleotide RNAs," Genes & Development, 2001, pp. 188-200, vol. 15.
Fire, A., "RNA-triggered Gene Silencing," Trends in Genetics, Sep. 1999, pp. 358-363, vol. 15, No. 9.
Fire, A., et al., "Potent and Specific Genetic Interference by Double Stranded RNA in *Caenorhabditis elegans*," Nature, Feb. 19, 1998, pp. 806-811, vol. 391.
Reynolds, et al. (2004) "Rational siRNA design for RNA interference," Nature Biotechnology, vol. 22, No. 3, pp. 326-330.
Robbins, M., et al., "Stable expression of shRNAs in human CD34+ progenitor cells can avoid induction of interferon responses to siRNAs in vitro," Nature Biotechnology, May 2006, pp. 566-571, vol. 24, No. 5.
Rose, S., et al., "Functional polarity is introduced by Dicer processing of short substrate RNAs," Nucleic Acids Research, 2005, pp. 4140-4156, vol. 33, No. 13.
Tuschl, T., "Functional genomics: RNA sets the standard," Nature, Jan. 16, 2003, vol. 421, No. 6920, pp. 220-221.
Tuschl T., "RNA Interference and Small Interfering RNAs" Chembiochem, 2001, pp. 239-245, vol. 2.
Tuschl, T., et al., "Small Interfering RNAs: A Revolutionary Tool for the Analysis of Gene Function and Gene Therapy," Molecular Interventions, 2002, pp. 158-167, vol. 2, No. 3.
Tuschl, T., "Mammalian RNA Interference," RNAi, A Guide to Gene Silencing, Chapter 13, G.J. Hannon (ed,), 2003, pp. 265-295.
Tuschl, T., et al., "Targeted mRNA Degradation by Double-Stranded RNA in Vitro," Genes & Development, 1999, pp. 3191-3197, vol. 13.
Tuschl, T., "Expanding small RNA interference," Nature Biotechnology, May 2002, pp. 446-448, vol. 20.
Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.
Weil, et al (2002) "Targeting the Kinesin Eg5 to Monitor siRNA Transfection in Mammalian Cells," *Biotechniques* 33(6):1244-1248.
Zimmerman, et al. (2006) "RNAi-mediated gene silencing in non-human primates," *Nature*, vol. 441, May 4: 111-114.

*Primary Examiner* — Kimberly Chong
(74) *Attorney, Agent, or Firm* — Fenwick & West LLP

(57) ABSTRACT

The present invention is based on the in vivo demonstration that RSV can be inhibited through intranasal administration of iRNA agents as well as by parenteral administration of such agents. Further, it is shown that effective viral reduction can be achieved with more than one virus being treated concurrently. Based on these findings, the present invention provides general and specific compositions and methods that are useful in reducing RSV mRNA levels, RSV protein levels and viral titers in a subject, e.g., a mammal, such as a human. These findings can be applied to other respiratory viruses.

19 Claims, 10 Drawing Sheets

In vitro silencing of RSV by siRNAs

FIG. 1

FIG. 2 siRNA targeting RSV genes show activity at very low dose in vitro

FIG. 3

In Vitro inhibition with siRNAs targeting RSV B subtype

FIG. 7 siRNAs inhibit RSV Replication Post-infection

Log10 PFU/g lung

Day 1
Day 2
Day 3
Day 4

PBS  2003  2017  2046  mt1730

RNAI MODULATION OF RSV AND THERAPEUTIC USES THEREOF

RELATED APPLICATIONS

This application is a continuation of U.S. application Ser. No. 12/021,245, filed Jan. 28, 2008, which is a is a continuation-in-part of U.S. application Ser. No. 11/411,291, filed on Apr. 26, 2006, now U.S. Pat. No. 7,517,865, issued on Apr. 14, 2009, which is a continuation-in-part of U.S. application Ser. No. 11/326,956, filed Jan. 6, 2006, now U.S. Pat. No. 7,507,809, issued on Mar. 24, 2009, which claims the benefit of U.S. Provisional Application No. 60/642,364, filed Jan. 7, 2005, and U.S. Provisional Application No. 60/659,828, filed Mar. 9, 2005. The entire contents of these priority applications are incorporated herein by reference.

TECHNICAL FIELD

The invention relates to the field of respiratory syncytial viral (RSV) therapy and compositions and methods for modulating viral replication, and more particularly to the down-regulation of a gene(s) of a respiratory syncytial virus by oligonucleotides via RNA interference which are administered locally to the lungs and nasal passage via inhalation/intranasally or systemically via injection/intravenous.

REFERENCE TO SEQUENCE LISTING

This application includes a Sequence Listing submitted electronically as a text file named 20765_sequence_listing.txt, created on Mar. 14, 2012, with a size of 78,177 bytes. The sequence listing is incorporated by reference.

BACKGROUND

By virtue of its natural function the respiratory tract is exposed to a slew of airborne pathogens that cause a variety of respiratory ailments. Viral infection of the respiratory tract is the most common cause of infantile hospitalization in the developed world with an estimated 91,000 annual admissions in the US at a cost of $300 M. Human respiratory syncytial virus (RSV) and parainfluenza virus (PIV) are two major agents of respiratory illness; together, they infect the upper and lower respiratory tracts, leading to croup, pneumonia and bronchiolitis (Openshaw, P. J. M. Respir. Res. 3 (Suppl 1), S15-S20 (2002), Easton, A. J., et al., Clin. Microbiol. Rev. 17, 390-412 (2004)). RSV alone infects up to 65% of all babies within the first year of life, and essentially all within the first 2 years. It is a significant cause of morbidity and mortality in the elderly as well. Immunity after RSV infection is neither complete nor lasting, and therefore, repeated infections occur in all age groups. Infants experiencing RSV bronchiolitis are more likely to develop wheezing and asthma later in life. Research for effective treatment and vaccine against RSV has been ongoing for nearly four decades with few successes (Openshaw, P. J. M. Respir. Res. 3 (Suppl 1), S15-S20 (2002), Maggon, K. et al, Rev. Med. Virol. 14, 149-168 (2004)). Currently, no vaccine is clinically approved for either RSV. Strains of both viruses also exist for nonhuman animals such as the cattle, goat, pig and sheep, causing loss to agriculture and the dairy and meat industry (Easton, A. J., et al., Clin. Microbiol. Rev. 17, 390-412 (2004)).

Both RSV contain nonsegmented negative-strand RNA genomes and belong to the Paramyxoviridae family. A number of features of these viruses have contributed to the difficulties of prevention and therapy. The viral genomes mutate at a high rate due to the lack of a replicational proof-reading mechanism of the RNA genomes, presenting a significant challenge in designing a reliable vaccine or antiviral (Sullender, W. M. Clin. Microbiol. Rev. 13, 1-15 (2000)). Promising inhibitors of the RSV fusion protein (F) were abandoned partly because the virus developed resistant mutations that were mapped to the F gene (Razinkov, V., et. al., Antivir. Res. 55, 189-200 (2002), Morton, C. J. et al. Virology 311, 275-288 (2003)). Both viruses associate with cellular proteins, adding to the difficulty of obtaining cell-free viral material for vaccination (Burke, E., et al., Virology 252, 137-148 (1998), Burke, E., et al., J. Virol. 74, 669-675 (2000), Gupta, S., et al., J. Virol. 72, 2655-2662 (1998)). Finally, the immunology of both, and especially that of RSV, is exquisitely complex (Peebles, R. S., Jr., et al., Viral. Immunol. 16, 25-34 (2003), Haynes, L. M., et al., J. Virol. 77, 9831-9844 (2003)). Use of denatured RSV proteins as vaccines leads to "immunopotentiation" or vaccine-enhanced disease (Polack, F. P. et al. J. Exp. Med. 196, 859-865 (2002)). The overall problem is underscored by the recent closure of a number of anti-RSV biopharma programs.

The RSV genome comprises a single strand of negative sense RNA that is 15,222 nucleotides in length and yields eleven major proteins. (Falsey, A. R., and E. E. Walsh, 2000, Clinical Microbiological Reviews 13:371-84.) Two of these proteins, the F (fusion) and G (attachment) glycoproteins, are the major surface proteins and the most important for inducing protective immunity. The SH (small hydrophobic) protein, the M (matrix) protein, and the M2 (22 kDa) protein are associated with the viral envelope but do not induce a protective immune response. The N (major nucleocapsid associated protein), P (phosphoprotein), and L (major polymerase protein) proteins are found associated with virion RNA. The two non-structural proteins, NS1 and NS2, presumably participate in host-virus interaction but are not present in infectious virions.

Human RSV strains have been classified into two major groups, A and B. The G glycoprotein has been shown to be the most divergent among RSV proteins. Variability of the RSV G glycoprotein between and within the two RSV groups is believed to be important to the ability of RSV to cause yearly outbreaks of disease. The G glycoprotein comprises 289-299 amino acids (depending on RSV strain), and has an intracellular, transmembrane, and highly glycosylated stalk structure of 90 kDa, as well as heparin-binding domains. The glycoprotein exists in secreted and membrane-bound forms.

Successful methods of treating RSV infection are currently unavailable (Maggon K and S. Barik, 2004, Reviews in Medical Virology 14:149-68). Infection of the lower respiratory tract with RSV is a self-limiting condition in most cases. No definitive guidelines or criteria exist on how to treat or when to admit or discharge infants and children with the disease. Hypoxia, which can occur in association with RSV infection, can be treated with oxygen via a nasal cannula. Mechanical ventilation for children with respiratory failure, shock, or recurrent apnea can lower mortality. Some physicians prescribe steroids. However, several studies have shown that steroid therapy does not affect the clinical course of infants and children admitted to the hospital with bronchiolitis. Thus corticosteroids, alone or in combination with bronchodilators, may be useless in the management of bronchiolitis in otherwise healthy unventilated patients. In infants and children with underlying cardiopulmonary diseases, such as bronchopulmonary dysphasia and asthma, steroids have also been used.

Ribavirin, a guanosine analogue with antiviral activity, has been used to treat infants and children with RSV bronchiolitis since the mid 1980s, but many studies evaluating its use have shown conflicting results. In most centers, the use of ribavirin is now restricted to immunocompromised patients and to those who are severely ill.

The severity of RSV bronchiolitis has been associated with low serum retinol concentrations, but trials in hospitalized children with RSV bronchiolitis have shown that vitamin A supplementation provides no beneficial effect. Therapeutic trials of 1500 mg/kg intravenous RSV immune globulin or 100 mg/kg inhaled immune globulin for RSV lower-respiratory-tract infection have also failed to show substantial beneficial effects.

In developed countries, the treatment of RSV lower-respiratory-tract infection is generally limited to symptomatic therapy. Antiviral therapy is usually limited to life-threatening situations due to its high cost and to the lack of consensus on efficacy. In developing countries, oxygen is the main therapy (when available), and the only way to lower mortality is through prevention.

RNA interference or "RNAi" is a term initially coined by Fire and co-workers to describe the observation that double-stranded RNA (dsRNA) can block gene expression when it is introduced into worms (Fire et al., *Nature* 391:806-811, 1998). Short dsRNA directs gene-specific, post-transcriptional silencing in many organisms, including vertebrates, and has provided a new tool for studying gene function. RNAi has been suggested as a method of developing a new class of therapeutic agents. However, to date, these have remained mostly as suggestions with no demonstrate proof that RNAi can be used therapeutically.

Therefore, there is a need for safe and effective vaccines against RSV, especially for infants and children. There is also a need for therapeutic agents and methods for treating RSV infection at all ages and in immuno-compromised individuals. There is also a need for scientific methods to characterize the protective immune response to RSV so that the pathogenesis of the disease can be studied, and screening for therapeutic agents and vaccines can be facilitated. The present invention overcomes previous shortcomings in the art by providing methods and compositions effective for modulating or preventing RSV infection. Specifically, the present invention advances the art by providing iRNA agents that have been shown to reduce RSV levels in vitro and in vivo, as well as being effective against both major subtypes of RSV, and a showing of therapeutic activity of this class of molecules.

SUMMARY

The present invention is based on the in vitro and in vivo demonstration that RSV can be inhibited through intranasal administration of iRNA agents, as well as by parenteral administration of such agents, and the identification of potent iRNA agents from the P, N and L gene of RSV that can reduce RNA levels with both the A and B subtype of RSV. Based on these findings, the present invention provides specific compositions and methods that are useful in reducing RSV mRNA levels, RSV protein levels and RSV viral titers in a subject, e.g., a mammal, such as a human.

In one aspect, the invention features an iRNA agent comprising two oligonucleotide sequences selected from those listed in Tables 1(a)-1(c). In one embodiment, the iRNA agent comprises an oligonucleotide consisting of the sequence of SEQ ID NO:267, where the oligonucleotide is obtained by removing a silyl protecting group from an oligonucleotide precursor, where removal includes the steps of admixing the oligonucleotide precursor of SEQ ID NO:267 with pyridine-HF, DMAP-HF, Urea-HF, TSAF, DAST, polyvinyl pyridine-HF or an aryl amine-HF reagent of formula AA:

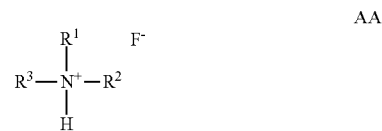

where
$R^1$ is alkyl, aryl, heteroaryl, aralkyl or heteroaralkyl;
$R^2$ is alkyl, aryl, heteroaryl, aralkyl or heteroaralkyl; and
$R^3$ is aryl or heteroaryl.

In another aspect, the invention provides a method of making an isolated oligonucleotide consisting of a sequence described in Tables 1(a)-1(c), where the method includes obtaining an oligonucleotide precursor bearing a silyl protecting group and admixing the oligonucleotide precursor with pyridine-HF, DMAP-HF, Urea-HF, TSAF, DAST, polyvinyl pyridine-HF or an aryl amine-HF reagent of formula AA:

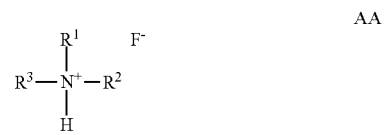

where
$R^1$ is alkyl, aryl, heteroaryl, aralkyl or heteroaralkyl;
$R^2$ is alkyl, aryl, heteroaryl, aralkyl or heteroaralkyl; and
$R^3$ is aryl or heteroaryl In one embodiment, the isolated oligonucleotide has the sequence of SEQ ID NO:267.

The present invention also provides iRNA agents consisting of, consisting essentially of or comprising at least 15 or more contiguous nucleotides of one of the genes of RSV, particularly the P, N and L genes of RSV, and more particularly agents that comprising 15 or more contiguous nucleotides from one of the sequence provided in Table 1 (a-c). The iRNA agent preferably consists of less than 30 nucleotides per strand, e.g., 21-23 nucleotides, such as those provided in Tables 1 (a-c). The double stranded iRNA agent can either have blunt ends or more preferably have overhangs of 1-4 nucleotides from one or both 3' ends of the agent.

Further, the iRNA agent can either contain only naturally occurring ribonucleotide subunits, or can be synthesized so as to contain one or more modifications to the sugar or base of one or more of the ribonucleotide subunits that is included in the agent. The iRNA agent can be further modified so as to be attached to a ligand that is selected to improve stability, distribution or cellular uptake of the agent, e.g. cholesterol. The iRNA agents can further be in isolated form or can be part of a pharmaceutical composition used for the methods described herein, particularly as a pharmaceutical composition formulated for delivery to the lungs or nasal passage or formulated for parental administration. The pharmaceutical compositions can contain one or more iRNA agents, and in some embodiments, will contain two or more iRNA agents, each one directed to a different segment of a RSV gene or to two different RSV genes.

The present invention further provides methods for reducing the level of RSV viral mRNA in a cell. Such methods comprise the step of administering one of the iRNA agents of the present invention to a subject as further described below. The present methods utilize the cellular mechanisms involved in RNA interference to selectively degrade the viral mRNA in a cell and are comprised of the step of contacting a cell with one of the antiviral iRNA agents of the present invention. Such methods can be performed directly on a cell or can be performed on a mammalian subject by administering to a subject one of the iRNA agents/pharmaceutical compositions of the present invention. Reduction of viral mRNA in a cells results in a reduction in the amount of viral protein produced, and in an organism, results in a decrease in replicating viral titer (as shown in the Examples).

The methods and compositions of the invention, e.g., the methods and iRNA agent compositions can be used with any dosage and/or formulation described herein, as well as with any route of administration described herein. Particularly important is the showing herein of intranasal administration of an iRNA agent and its ability to inhibit viral replication in respiratory tissues.

One or both strands of strand an iRNA agent can be isolated according to methods described in PCT publication No. WO2005/097817, which is incorporated herein by reference in its entirety.

The details of one or more embodiments of the invention are set forth in the accompanying drawings and the description below. Other features, objects, and advantages of the invention will be apparent from this description, the drawings, and from the claims. This application incorporates all cited references, patents, and patent applications by references in their entirety for all purposes.

BRIEF DESCRIPTION OF DRAWINGS

Figure 1:
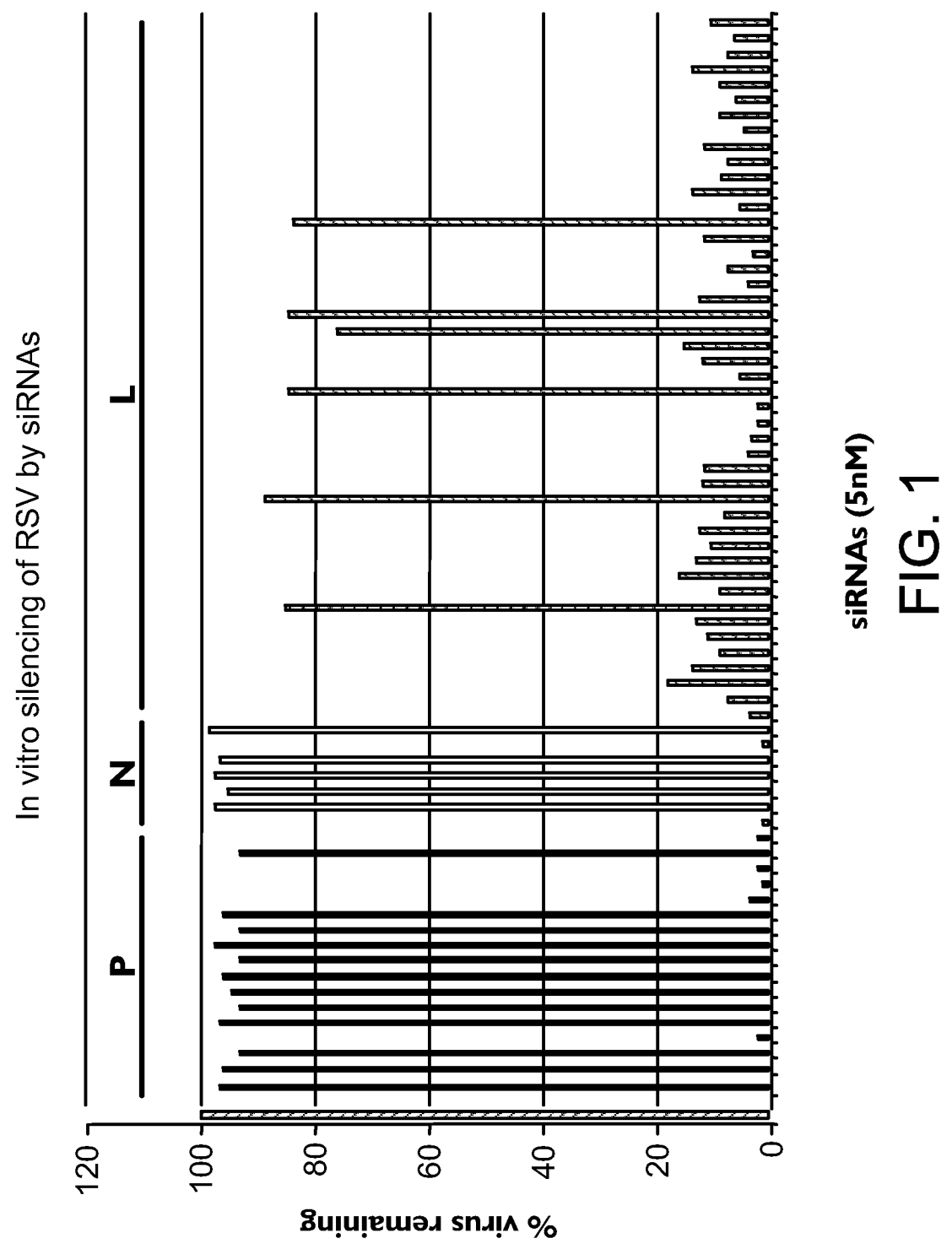

FIG. 1: In vitro inhibition of RSV using iRNA agents. iRNA agents provided in Table 1 (a-c) were tested for anti-RSV activity in a plaque formation assay as described in the Examples. Each column (bar) represents an iRNA agent provided in Table 1 (a-c), e.g. column 1 is the first agent in Table 1a etc. Active iRNA agents were identified.

FIG. 2: In vitro dose response inhibition of RSV using iRNA agents. Examples of active agents from Table 1 were tested for anti-RSV activity in a plaque formation assay as described in the Examples at four concentrations. A dose dependent response was found with active iRNA agent tested.

FIG. 3: In vitro inhibition of RSV B subtype using iRNA agents. iRNA agents provided in FIG. 2 were tested for anti-RSV activity against subtype B in a plaque formation assay as described in the Examples. Subtype B was inhibited by the iRNA agents tested.

FIG. 4: In vivo inhibition of RSV using iRNA agents. Agents as described in the figure were tested for anti-RSV activity in a mouse model as described in the Examples. The iRNA agents were effective at reducing viral titers in vivo.

Figure 6:
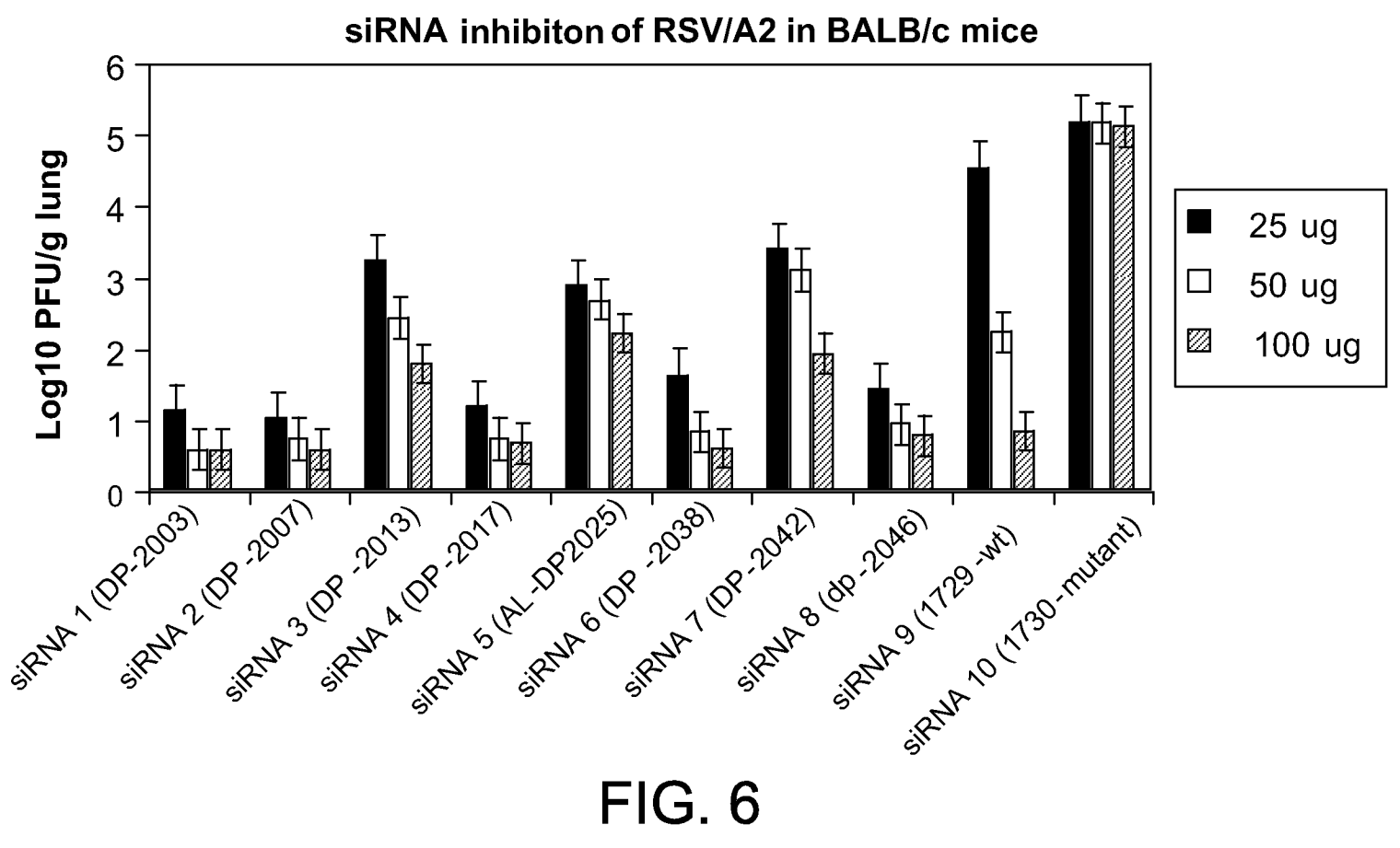

FIG. 6: In vivo inhibition of RSV using iRNA agents. iRNA agents described in the Figure were tested for anti-RSV activity in vivo as described in the Examples.

FIG. 7: In vivo inhibition of RSV using iRNA agents. iRNA agents described in the Figure were tested for anti-RSV activity in vivo as described in the Examples.

DETAILED DESCRIPTION

Figure 5:
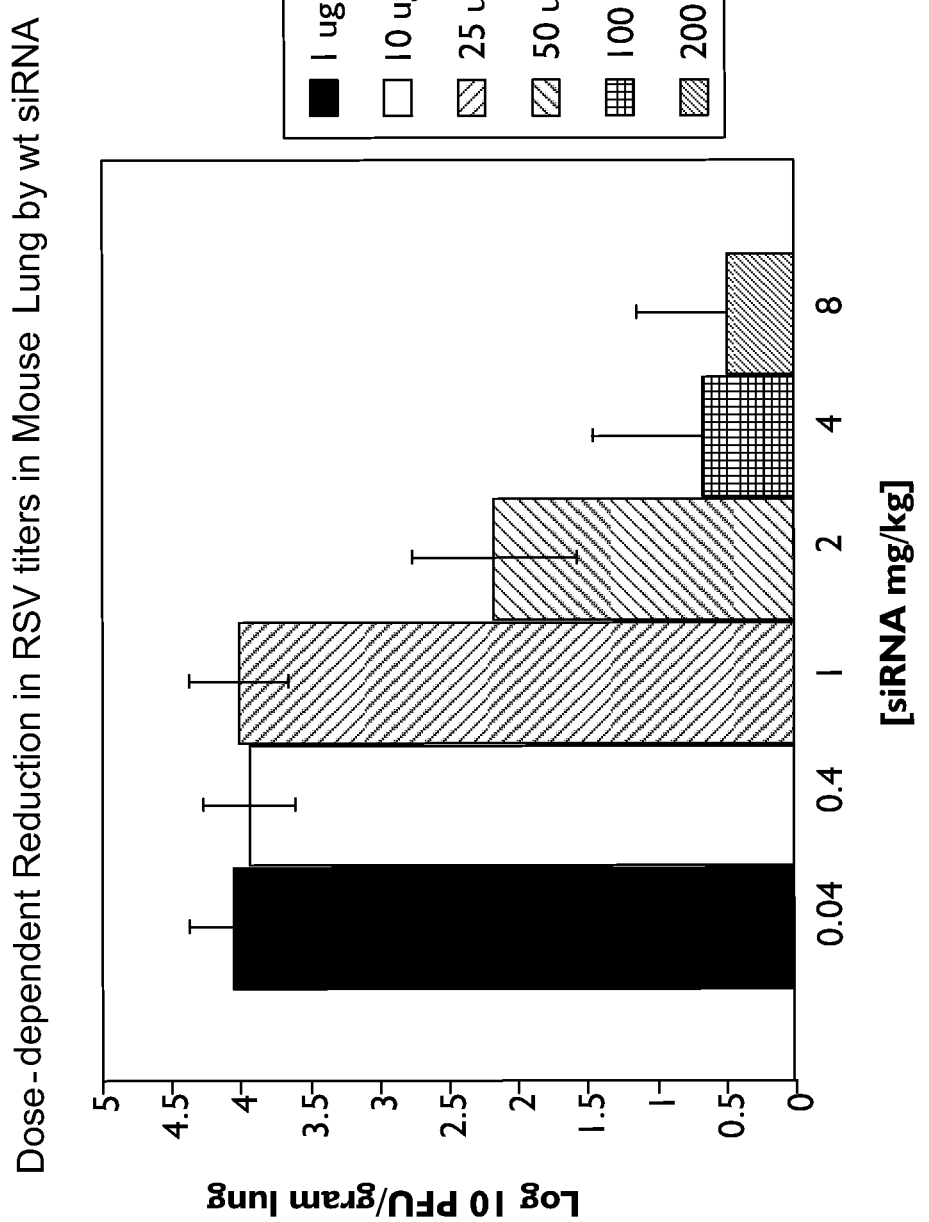
FIG. 5: In vivo inhibition of RSV using AL-DP-1730. AL-DP-1730 was tested for dose dependent activity using the methods provided in the Examples. The agents showed a dose dependent response.

For ease of exposition the term "nucleotide" or "ribonucleotide" is sometimes used herein in reference to one or more monomeric subunits of an RNA agent. It will be understood that the usage of the term "ribonucleotide" or "nucleotide" herein can, in the case of a modified RNA or nucleotide surrogate, also refer to a modified nucleotide, or surrogate replacement moiety, as further described below, at one or more positions.

An "RNA agent" as used herein, is an unmodified RNA, modified RNA, or nucleoside surrogate, all of which are described herein or are well known in the RNA synthetic art. While numerous modified RNAs and nucleoside surrogates are described, preferred examples include those which have greater resistance to nuclease degradation than do unmodified RNAs. Preferred examples include those that have a 2' sugar modification, a modification in a single strand overhang, preferably a 3' single strand overhang, or, particularly if single stranded, a 5'-modification which includes one or more phosphate groups or one or more analogs of a phosphate group.

An "iRNA agent" (abbreviation for "interfering RNA agent") as used herein, is an RNA agent, which can down-regulate the expression of a target gene, e.g., RSV. While not wishing to be bound by theory, an iRNA agent may act by one or more of a number of mechanisms, including post-transcriptional cleavage of a target mRNA sometimes referred to in the art as RNAi, or pre-transcriptional or pre-translational mechanisms. An iRNA agent can be a double stranded (ds) iRNA agent.

A "ds iRNA agent" (abbreviation for "double stranded iRNA agent"), as used herein, is an iRNA agent which includes more than one, and preferably two, strands in which interchain hybridization can form a region of duplex structure. A "strand" herein refers to a contiguouous sequence of nucleotides (including non-naturally occurring or modified nucleotides). The two or more strands may be, or each form a part of, separate molecules, or they may be covalently interconnected, e.g. by a linker, e.g. a polyethyleneglycol linker, to form but one molecule. At least one strand can include a region which is sufficiently complementary to a target RNA. Such strand is termed the "antisense strand". A second strand comprised in the dsRNA agent which comprises a region complementary to the antisense strand is termed the "sense strand". However, a ds iRNA agent can also be formed from a single RNA molecule which is, at least partly; self-complementary, forming, e.g., a hairpin or panhandle structure, including a duplex region. In such case, the term "strand" refers to one of the regions of the RNA molecule that is complementary to another region of the same RNA molecule.

Although, in mammalian cells, long ds iRNA agents can induce the interferon response which is frequently deleterious, short ds iRNA agents do not trigger the interferon response, at least not to an extent that is deleterious to the cell and/or host. The iRNA agents of the present invention include molecules which are sufficiently short that they do not trigger a deleterious interferon response in mammalian cells. Thus, the administration of a composition of an iRNA agent (e.g., formulated as described herein) to a mammalian cell can be used to silence expression of an RSV gene while circumventing a deleterious interferon response. Molecules that are short enough that they do not trigger a deleterious interferon response are termed siRNA agents or siRNAs herein. "siRNA agent" or "siRNA" as used herein, refers to an iRNA agent, e.g., a ds iRNA agent, that is sufficiently short that it does not induce a deleterious interferon response in a human cell, e.g., it has a duplexed region of less than 30 nucleotide pairs.

The isolated iRNA agents described herein, including ds iRNA agents and siRNA agents, can mediate silencing of a gene, e.g., by RNA degradation. For convenience, such RNA is also referred to herein as the RNA to be silenced. Such a gene is also referred to as a target gene. Preferably, the RNA to be silenced is a gene product of an RSV gene, particularly the P, N or L gene product.

As used herein, the phrase "mediates RNAi" refers to the ability of an agent to silence, in a sequence specific manner, a target gene. "Silencing a target gene" means the process whereby a cell containing and/or secreting a certain product of the target gene when not in contact with the agent, will contain and/or secret at least 10%, 20%, 30%, 40%, 50%, 60%, 70%, 80%, or 90% less of such gene product when contacted with the agent, as compared to a similar cell which has not been contacted with the agent. Such product of the target gene can, for example, be a messenger RNA (mRNA), a protein, or a regulatory element.

In the anti viral uses of the present invention, silencing of a target gene will result in a reduction in "viral titer" in the cell or in the subject. As used herein, "reduction in viral titer" refers to a decrease in the number of viable virus produced by a cell or found in an organism undergoing the silencing of a viral target gene. Reduction in the cellular amount of virus produced will preferably lead to a decrease in the amount of measurable virus produced in the tissues of a subject undergoing treatment and a reduction in the severity of the symptoms of the viral infection. iRNA agents of the present invention are also referred to as "antiviral iRNA agents".

As used herein, a "RSV gene" refers to any one of the genes identified in the RSV virus genome (See Falsey, A. R., and E. E. Walsh, 2000, Clinical Microbiological Reviews 13:371-84). These genes are readily known in the art and include the N, P and L genes which are exemplified herein.

As used herein, the term "complementary" is used to indicate a sufficient degree of complementarity such that stable and specific binding occurs between a compound of the invention and a target RNA molecule, e.g. an RSV viral mRNA molecule. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 4 nucleotides.

As used herein, an iRNA agent is "sufficiently complementary" to a target RNA, e.g., a target mRNA (e.g., a target RSV mRNA) if the iRNA agent reduces the production of a protein encoded by the target RNA in a cell. The iRNA agent may also be "exactly complementary" to the target RNA, e.g., the target RNA and the iRNA agent anneal, preferably to form a hybrid made exclusively of Watson-Crick base pairs in the region of exact complementarity. A "sufficiently complementary" iRNA agent can include an internal region (e.g., of at least 10 nucleotides) that is exactly complementary to a target viral RNA. Moreover, in some embodiments, the iRNA agent specifically discriminates a single-nucleotide difference. In this case, the iRNA agent only mediates RNAi if exact complementarity is found in the region (e.g., within 7 nucleotides of) the single-nucleotide difference. Preferred iRNA agents will be based on or consist or comprise the sense and antisense sequences provided in the Examples.

As used herein, "essentially identical" when used referring to a first nucleotide sequence in comparison to a second nucleotide sequence means that the first nucleotide sequence is identical to the second nucleotide sequence except for up to one, two or three nucleotide substitutions (e.g. adenosine replaced by uracil).

As used herein, a "subject" refers to a mammalian organism undergoing treatment for a disorder mediated by viral expression, such as RSV infection or undergoing treatment prophylactically to prevent viral infection. The subject can be any mammal, such as a primate, cow, horse, mouse, rat, dog, pig, goat. In the preferred embodiment, the subject is a human.

As used herein, treating RSV infection refers to the amelioration of any biological or pathological endpoints that 1) is mediated in part by the presence of the virus in the subject and 2) whose outcome can be affected by reducing the level of viral gene products present.

Design and Selection of iRNA Agents

The present invention is based on the demonstration of target gene silencing of a respiratory viral gene in vivo following local administration to the lungs and nasal passage of an iRNA agent either via intranasal administration/inhalation or systemically/parenterally via injection and the resulting treatment of viral infection. The present invention is further extended to the use of iRNA agents to more than one respiratory virus and the treatment of both virus infections with co-administration of two or more iRNA agents.

Based on these results, the invention specifically provides an iRNA agent that can be used in treating viral infection, particularly respiratory viruses and in particular RSV infection, in isolated form and as a pharmaceutical composition described below. Such agents will include a sense strand having at least 15 or more contiguous nucleotides that are complementary to a viral gene and an antisense strand having at least 15 or more contiguous nucleotides that are complementary to the sense strand sequence. Particularly useful are iRNA agents that consist of, consist essentially of or comprise a nucleotide sequence from the P N and L gene of RSV as provided in Table 1 (a-c).

The iRNA agents of the present invention are based on and comprise at least 15 or more contiguous nucleotides from one of the iRNA agents shown to be active in Table 1 (a-c). In such agents, the agent can consist of consist essentially of or comprise the entire sequence provided in the table or can comprise 15 or more contiguous residues provided in Tablela-c along with additional nucleotides from contiguous regions of the target gene.

An iRNA agent can be rationally designed based on sequence information and desired characteristics and the information provided in Table 1 (a-c). For example, an iRNA agent can be designed according to sequence of the agents provided in the Tables as well as in view of the entire coding sequence of the target gene.

Accordingly, the present invention provides iRNA agents comprising a sense strand and antisense strand each comprising a sequence of at least 15, 16, 17, 18, 19, 20, 21 or 23 nucleotides which is essentially identical to, as defined above, a portion of a gene from a respiratory virus, particularly the P, N or L protein genes of RSV. Exemplified iRNA agents include those that comprise 15 or more contiguous nucleotides from one of the agents provided in Table 1 (a-c).

The antisense strand of an iRNA agent should be equal to or at least, 15, 16, 17, 18, 19, 25, 29, 40, or 50 nucleotides in length. It should be equal to or less than 50, 40, or 30, nucleotides in length. Preferred ranges are 15-30, 17 to 25, 19 to 23, and 19 to 21 nucleotides in length. Exemplified iRNA agents include those that comprise 15 or more nucleotides from one of the antisense strands of one of the agents in Table 1 (a-c).

The sense strand of an iRNA agent should be equal to or at least 15, 16, 17, 18, 19, 25, 29, 40, or 50 nucleotides in length. It should be equal to or less than 50, 40, or 30 nucleotides in length. Preferred ranges are 15-30, 17 to 25, 19 to 23, and 19 to 21 nucleotides in length. Exemplified iRNA agents include those that comprise 15 or more nucleotides from one of the sense strands of one of the agents in Table 1 (a-c).

The double stranded portion of an iRNA agent should be equal to or at least, 15, 16, 17, 18, 19, 20, 21, 22, 23, 24, 25, 29, 40, or 50 nucleotide pairs in length. It should be equal to or less than 50, 40, or 30 nucleotides pairs in length. Preferred ranges are 15-30, 17 to 25, 19 to 23, and 19 to 21 nucleotides pairs in length.

The agents provided in Table 1 (a-c) are 21 nucleotide in length for each strand. The iRNA agents contain a 19 nucleotide double stranded region with a 2 nucleotide overhang on each of the 3' ends of the agent. These agents can be modified as described herein to obtain equivalent agents comprising at least a portion of these sequences (15 or more contiguous nucleotides) and or modifications to the oligonucleotide bases and linkages.

Generally, the iRNA agents of the instant invention include a region of sufficient complementarity to the viral gene, e.g. the P, N or L protein of RSV, and are of sufficient length in terms of nucleotides, that the iRNA agent, or a fragment thereof, can mediate down regulation of the specific viral gene. The antisense strands of the iRNA agents of the present invention are preferably fully complementary to the mRNA sequences of viral gene, as is herein for the P, L or N proteins of RSV. However, it is not necessary that there be perfect complementarity between the iRNA agent and the target, but the correspondence must be sufficient to enable the iRNA agent, or a cleavage product thereof, to direct sequence specific silencing, e.g., by RNAi cleavage of an RSV mRNA.

Therefore, the iRNA agents of the instant invention include agents comprising a sense strand and antisense strand each comprising a sequence of at least 16, 17 or 18 nucleotides which is essentially identical, as defined below, to one of the sequences of a viral gene, particularly the P, N or L protein of RSV, such as those agent provided in Table 1 (a-c), except that not more than 1, 2 or 3 nucleotides per strand, respectively, have been substituted by other nucleotides (e.g. adenosine replaced by uracil), while essentially retaining the ability to inhibit RSV expression in cultured human cells, as defined below. These agents will therefore possess at least 15 or more nucleotides identical to one of the sequences of a viral gene, particularly the P, L or N protein gene of RSV, but 1, 2 or 3 base mismatches with respect to either the target viral mRNA sequence or between the sense and antisense strand are introduced. Mismatches to the target viral mRNA sequence, particularly in the antisense strand, are most tolerated in the terminal regions and if present are preferably in a terminal region or regions, e.g., within 6, 5, 4, or 3 nucleotides of a 5' and/or 3' terminus, most preferably within 6, 5, 4, or 3 nucleotides of the 5'-terminus of the sense strand or the 3'-terminus of the antisense strand. The sense strand need only be sufficiently complementary with the antisense strand to maintain the overall double stranded character of the molecule.

It is preferred that the sense and antisense strands be chosen such that the iRNA agent includes a single strand or unpaired region at one or both ends of the molecule, such as those exemplified in Table 1 (a-c). Thus, an iRNA agent contains sense and antisense strands, preferably paired to contain an overhang, e.g., one or two 5' or 3' overhangs but preferably a 3' overhang of 2-3 nucleotides. Most embodiments will have a 3' overhang. Preferred siRNA agents will have single-stranded overhangs, preferably 3' overhangs, of 1 to 4, or preferably 2 or 3 nucleotides, in length, on one or both ends of the iRNA agent. The overhangs can be the result of one strand being longer than the other, or the result of two strands of the same length being staggered. 5'-ends are preferably phosphorylated.

Preferred lengths for the duplexed region is between 15 and 30, most preferably 18, 19, 20, 21, 22, and 23 nucleotides in length, e.g., in the siRNA agent range discussed above. Embodiments in which the two strands of the siRNA agent are linked, e.g., covalently linked are also included. Hairpin, or other single strand structures which provide the required double stranded region, and preferably a 3' overhang are also within the invention.

Evaluation of Candidate iRNA Agents

A candidate iRNA agent can be evaluated for its ability to down regulate target gene expression. For example, a candidate iRNA agent can be provided, and contacted with a cell, e.g. a human cell, that has been infected with or will be infected with the virus of interest, e.g., a virus containing the target gene. Alternatively, the cell can be transfected with a construct from which a target viral gene is expressed, thus preventing the need for a viral infectivity model. The level of target gene expression prior to and following contact with the candidate iRNA agent can be compared, e.g. on an RNA, protein level or viral titer. If it is determined that the amount of RNA, protein or virus expressed from the target gene is lower following contact with the iRNA agent, then it can be concluded that the iRNA agent down-regulates target gene expression. The level of target viral RNA or viral protein in the cell or viral titer in a cell or tissue can be determined by any method desired. For example, the level of target RNA can be determined by Northern blot analysis, reverse transcription coupled with polymerase chain reaction (RT-PCR), bDNA analysis, or RNAse protection assay. The level of protein can be determined, for example, by Western blot analysis or immuno-fluorescence. Viral titer can be detected through a plaque formation assay.

Stability Testing, Modification, and Retesting of iRNA Agents

A candidate iRNA agent can be evaluated with respect to stability, e.g., its susceptibility to cleavage by an endonuclease or exonuclease, such as when the iRNA agent is introduced into the body of a subject. Methods can be employed to identify sites that are susceptible to modification, particularly cleavage, e.g., cleavage by a component found in the body of a subject.

When sites susceptible to cleavage are identified, a further iRNA agent can be designed and/or synthesized wherein the potential cleavage site is made resistant to cleavage, e.g. by introduction of a 2'-modification on the site of cleavage, e.g. a 2'-O-methyl group. This further iRNA agent can be retested for stability, and this process may be iterated until an iRNA agent is found exhibiting the desired stability.

In Vivo Testing

An iRNA agent identified as being capable of inhibiting viral gene expression can be tested for functionality in vivo in an animal model (e.g., in a mammal, such as in mouse, rat or primate) as shown in the examples. For example, the iRNA agent can be administered to an animal, and the iRNA agent evaluated with respect to its biodistribution, stability, and its ability to inhibit viral, e.g. RSV, gene expression or reduce viral titer.

The iRNA agent can be administered directly to the target tissue, such as by injection, or the iRNA agent can be administered to the animal model in the same manner that it would be administered to a human. As shown herein, the agent can be preferably administered via inhalation as a means of treating viral infection.

The iRNA agent can also be evaluated for its intracellular distribution. The evaluation can include determining whether the iRNA agent was taken up into the cell. The evaluation can also include determining the stability (e.g., the half-life) of the iRNA agent. Evaluation of an iRNA agent in vivo can be facilitated by use of an iRNA agent conjugated to a traceable marker (e.g., a fluorescent marker such as fluorescein; a radioactive label, such as $^{35}S$, $^{32}P$, $^{33}P$, or $^{3}H$; gold particles; or antigen particles for immunohistochemistry) or other suitable detection method.

The iRNA agent can be evaluated with respect to its ability to down regulate viral gene expression. Levels of viral gene expression in vivo can be measured, for example, by in situ hybridization, or by the isolation of RNA from tissue prior to and following exposure to the iRNA agent. Where the animal needs to be sacrificed in order to harvest the tissue, an untreated control animal will serve for comparison. Target viral mRNA can be detected by any desired method, including but not limited to RT-PCR, Northern blot, branched-DNA assay, or RNAase protection assay. Alternatively, or additionally, viral gene expression can be monitored by performing Western blot analysis on tissue extracts treated with the iRNA agent or by ELISA. Viral titer can be determined using a pfu assy.

iRNA Chemistry

Described herein are isolated iRNA agents, e.g., ds RNA agents, that mediate RNAi to inhibit expression of a viral gene, e.g. the P protein of RSV.

RNA agents discussed herein include otherwise unmodified RNA as well as RNA which have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al., (1994) *Nucleic Acids Res.* 22: 2183-2196. Such rare or unusual RNAs, often termed modified RNAs (apparently because these are typically the result of a post-transcriptional modification) are within the term unmodified RNA, as used herein. Modified RNA as used herein refers to a molecule in which one or more of the components of the nucleic acid, namely sugars, bases, and phosphate moieties, are different from that which occurs in nature, preferably different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of each of the above are discussed herein.

Modifications described herein can be incorporated into any double-stranded RNA and RNA-like molecule described herein, e.g., an iRNA agent. It may be desirable to modify one or both of the antisense and sense strands of an iRNA agent. As nucleic acids are polymers of subunits or monomers, many of the modifications described below occur at a position which is repeated within a nucleic acid, e.g., a modification of a base, or a phosphate moiety, or the non-linking O of a phosphate moiety. In some cases the modification will occur at all of the subject positions in the nucleic acid but in many, and in fact in most, cases it will not. By way of example, a modification may only occur at a 3' or 5' terminal position, may only occur in a terminal region, e.g. at a position on a terminal nucleotide or in the last 2, 3, 4, 5, or 10 nucleotides of a strand. A modification may occur in a double strand region, a single strand region, or in both. E.g., a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. Similarly, a modification may occur on the sense strand, antisense strand, or both. In some cases, the sense and antisense strand will have the same modifications or the same class of modifications, but in other cases the sense and antisense strand will have different modifications, e.g., in some cases it may be desirable to modify only one strand, e.g. the sense strand.

Two prime objectives for the introduction of modifications into iRNA agents is their stabilization towards degradation in biological environments and the improvement of pharmacological properties, e.g. pharmacodynamic properties, which are further discussed below. Other suitable modifications to a sugar, base, or backbone of an iRNA agent are described in co-owned PCT Application No. PCT/US2004/01193, filed Jan. 16, 2004. An iRNA agent can include a non-naturally occurring base, such as the bases described in co-owned PCT Application No. PCT/US2004/011822, filed Apr. 16, 2004. An iRNA agent can include a non-naturally occurring sugar, such as a non-carbohydrate cyclic carrier molecule. Exemplary features of non-naturally occurring sugars for use in iRNA agents are described in co-owned PCT Application No. PCT/US2004/11829 filed Apr. 16, 2003.

An iRNA agent can include an internucleotide linkage (e.g., the chiral phosphorothioate linkage) useful for increasing nuclease resistance. In addition, or in the alternative, an iRNA agent can include a ribose mimic for increased nuclease resistance. Exemplary internucleotide linkages and ribose mimics for increased nuclease resistance are described in co-owned PCT Application No. PCT/US2004/07070 filed on Mar. 8, 2004.

An iRNA agent can include ligand-conjugated monomer subunits and monomers for oligonucleotide synthesis. Exemplary monomers are described in co-owned U.S. application Ser. No. 10/916,185, filed on Aug. 10, 2004.

An iRNA agent can have a ZXY structure, such as is described in co-owned PCT Application No. PCT/US2004/07070 filed on Mar. 8, 2004.

An iRNA agent can be complexed with an amphipathic moiety. Exemplary amphipathic moieties for use with iRNA agents are described in co-owned PCT Application No. PCT/US2004/07070 filed on Mar. 8, 2004.

In another embodiment, the iRNA agent can be complexed to a delivery agent that features a modular complex. The complex can include a carrier agent linked to one or more of (preferably two or more, more preferably all three of): (a) a condensing agent (e.g., an agent capable of attracting, e.g., binding, a nucleic acid, e.g., through ionic or electrostatic interactions); (b) a fusogenic agent (e.g., an agent capable of fusing and/or being transported through a cell membrane); and (c) a targeting group, e.g., a cell or tissue targeting agent, e.g., a lectin, glycoprotein, lipid or protein, e.g., an antibody, that binds to a specified cell type. iRNA agents complexed to a delivery agent are described in co-owned PCT Application No. PCT/US2004/07070 filed on Mar. 8, 2004.

An iRNA agent can have non-canonical pairings, such as between the sense and antisense sequences of the iRNA duplex. Exemplary features of non-canonical iRNA agents are described in co-owned PCT Application No. PCT/US2004/07070 filed on Mar. 8, 2004.

Enhanced Nuclease Resistance

An iRNA agent, e.g., an iRNA agent that targets RSV, can have enhanced resistance to nucleases.

For increased nuclease resistance and/or binding affinity to the target, an iRNA agent, e.g., the sense and/or antisense strands of the iRNA agent, can include, for example, 2'-modified ribose units and/or phosphorothioate linkages. E.g., the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE and aminoalkoxy, $O(CH_2)_n$AMINE, (e.g., AMINE=$NH_2$; alkylamino, dialkylamino, heterocyclyl amino, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl amino, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

Preferred substituents are 2'-methoxyethyl, 2'-OCH3, 2'-O-allyl, 2'-C-allyl, and 2'-fluoro.

One way to increase resistance is to identify cleavage sites and modify such sites to inhibit cleavage, as described in co-owned U.S. Application No. 60/559,917, filed on May 4, 2004. For example, the dinucleotides 5'-UA-3', 5'-UG-3', 5'-CA-3', 5'-UU-3', or 5'-CC-3' can serve as cleavage sites. Enhanced nuclease resistance can therefore be achieved by modifying the 5' nucleotide, resulting, for example, in at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3') dinucleotide, wherein the 5'-cytidine is a 2'-modified nucleotide. The iRNA agent can include at least 2, at least 3, at least 4 or at least 5 of such dinucleotides. In certain embodiments, all the pyrimidines of an iRNA agent carry a 2'-modification, and the iRNA agent therefore has enhanced resistance to endonucleases.

To maximize nuclease resistance, the 2' modifications can be used in combination with one or more phosphate linker modifications (e.g., phosphorothioate). The so-called "chimeric" oligonucleotides are those that contain two or more different modifications.

The inclusion of furanose sugars in the oligonucleotide backbone can also decrease endonucleolytic cleavage. An iRNA agent can be further modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of oligonucleotide. Even small alkyl chains, aryl groups, or heterocyclic conjugates or modified sugars (D-ribose, deoxyribose, glucose etc.) can block 3'-5'-exonucleases.

Similarly, 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of oligonucleotide. Even small alkyl chains, aryl groups, or heterocyclic conjugates or modified sugars (D-ribose, deoxyribose, glucose etc.) can block 3'-5'-exonucleases.

An iRNA agent can have increased resistance to nucleases when a duplexed iRNA agent includes a single-stranded nucleotide overhang on at least one end. In preferred embodiments, the nucleotide overhang includes 1 to 4, preferably 2 to 3, unpaired nucleotides. In a preferred embodiment, the unpaired nucleotide of the single-stranded overhang that is directly adjacent to the terminal nucleotide pair contains a purine base, and the terminal nucleotide pair is a G-C pair, or at least two of the last four complementary nucleotide pairs are G-C pairs. In further embodiments, the nucleotide overhang may have 1 or 2 unpaired nucleotides, and in an exemplary embodiment the nucleotide overhang is 5'-GC-3'. In preferred embodiments, the nucleotide overhang is on the 3'-end of the antisense strand. In one embodiment, the iRNA agent includes the motif 5'-CGC-3' on the 3'-end of the antisense strand, such that a 2-nt overhang 5'-GC-3' is formed.

Thus, an iRNA agent can include modifications so as to inhibit degradation, e.g., by nucleases, e.g., endonucleases or exonucleases, found in the body of a subject. These monomers are referred to herein as NRMs, or Nuclease Resistance promoting Monomers, the corresponding modifications as NRM modifications. In many cases these modifications will modulate other properties of the iRNA agent as well, e.g., the ability to interact with a protein, e.g., a transport protein, e.g., serum albumin, or a member of the RISC, or the ability of the first and second sequences to form a duplex with one another or to form a duplex with another sequence, e.g., a target molecule.

One or more different NRM modifications can be introduced into an iRNA agent or into a sequence of an iRNA agent. An NRM modification can be used more than once in a sequence or in an iRNA agent.

NRM modifications include some which can be placed only at the terminus and others which can go at any position. Some NRM modifications that can inhibit hybridization are preferably used only in terminal regions, and more preferably not at the cleavage site or in the cleavage region of a sequence which targets a subject sequence or gene, particularly on the antisense strand. They can be used anywhere in a sense strand, provided that sufficient hybridization between the two strands of the ds iRNA agent is maintained. In some embodiments it is desirable to put the NRM at the cleavage site or in the cleavage region of a sense strand, as it can minimize off-target silencing.

In most cases, the NRM modifications will be distributed differently depending on whether they are comprised on a sense or antisense strand. If on an antisense strand, modifications which interfere with or inhibit endonuclease cleavage should not be inserted in the region which is subject to RISC mediated cleavage, e.g., the cleavage site or the cleavage region (As described in Elbashir et al., 2001, Genes and Dev. 15: 188, hereby incorporated by reference). Cleavage of the target occurs about in the middle of a 20 or 21 nt antisense strand, or about 10 or 11 nucleotides upstream of the first nucleotide on the target mRNA which is complementary to the antisense strand. As used herein cleavage site refers to the nucleotides on either side of the site of cleavage, on the target mRNA or on the iRNA agent strand which hybridizes to it. Cleavage region means the nucleotides within 1, 2, or 3 nucleotides of the cleavage site, in either direction.

Such modifications can be introduced into the terminal regions, e.g., at the terminal position or with 2, 3, 4, or 5 positions of the terminus, of a sequence which targets or a sequence which does not target a sequence in the subject.

Tethered Ligands

The properties of an iRNA agent, including its pharmacological properties, can be influenced and tailored, for example, by the introduction of ligands, e.g. tethered ligands.

A wide variety of entities, e.g., ligands, can be tethered to an iRNA agent, e.g., to the carrier of a ligand-conjugated monomer subunit. Examples are described below in the context of a ligand-conjugated monomer subunit but that is only preferred, entities can be coupled at other points to an iRNA agent.

Preferred moieties are ligands, which are coupled, preferably covalently, either directly or indirectly via an intervening tether, to the carrier. In preferred embodiments, the ligand is attached to the carrier via an intervening tether. The ligand or tethered ligand may be present on the ligand-conjugated monomer when the ligand-conjugated monomer is incorporated into the growing strand. In some embodiments, the ligand may be incorporated into a "precursor" ligand-conjugated monomer subunit after a "precursor" ligand-conjugated monomer subunit has been incorporated into the growing strand. For example, a monomer having, e.g., an amino-terminated tether, e.g., TAP-$(CH_2)_n NH_2$ may be incorporated into a growing sense or antisense strand. In a subsequent operation, i.e., after incorporation of the precursor monomer subunit into the strand, a ligand having an electrophilic group, e.g., a pentafluorophenyl ester or aldehyde group, can subsequently be attached to the precursor ligand-conjugated monomer by coupling the electrophilic group of the ligand with the terminal nucleophilic group of the precursor ligand-conjugated monomer subunit tether.

In preferred embodiments, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand.

Preferred ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophilic moleculeses, lipids, lectins, steroids (e.g., uvaol, hecigenin, diosgenin), terpenes (e.g., triterpenes, e.g., sarsasapogenin, Friedelin, epifriedelanol derivatized lithocholic acid), vitamins, carbohydrates (e.g., a dextran, pullulan, chitin, chitosan, inulin, cyclodextrin or hyaluronic acid), proteins, protein binding agents, integrin targeting molecules, polycationics, peptides, polyamines, and peptide mimics.

The ligand may be a naturally occurring or recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha helical peptide.

Ligands can also include targeting groups, e.g., a cell or tissue targeting agent, e.g., a thyrotropin, melanotropin, surfactant protein A, Mucin carbohydrate, a glycosylated polyaminoacid, transferrin, bisphosphonate, polyglutamate, polyaspartate, or an RGD peptide or RGD peptide mimetic.

Ligands can be proteins, e.g., glycoproteins, lipoproteins, e.g. low density lipoprotein (LDL), or albumins, e.g. human serum albumin (HSA), or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as cofactors, multivalent lactose, multivalent galactose, N-acetyl-galactosamine, N-acetyl-glucosamine, multivalent mannose, or multivalent fucose. The ligand can be, for example, a lipopolysaccharide, an activator of p38 MAP kinase, or an activator of NF-κB.

The ligand can be a substance, e.g, a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In one aspect, the ligand is a lipid or lipid-based molecule. Such a lipid or lipid-based molecule preferably binds a serum protein, e.g., human serum albumin (HSA). Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another aspect, the ligand is a moiety, e.g., a vitamin or nutrient, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include the B vitamins, e.g., folic acid, B12, riboflavin, biotin, pyridoxal or other vitamins or nutrients taken up by cancer cells.

In another aspect, the ligand is a cell-permeation agent, preferably a helical cell-permeation agent. Preferably, the agent is amphipathic. An exemplary agent is a peptide such as tat or antennapedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

5'-Phosphate Modifications

In preferred embodiments, iRNA agents are 5' phosphorylated or include a phosphoryl analog at the 5' prime terminus 5'-phosphate modifications of the antisense strand include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure. Other suitable 5'-phosphate modifications will be known to the skilled person.

The sense strand can be modified in order to inactivate the sense strand and prevent formation of an active RISC, thereby potentially reducing off-target effects. This can be accomplished by a modification which prevents 5'-phosphorylation of the sense strand, e.g., by modification with a 5'-O-methyl ribonucleotide (see Nykanen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage.

Delivery of iRNA Agents to Tissues and Cells

Formulation

The iRNA agents described herein can be formulated for administration to a subject, preferably for administration locally to the lungs and nasal passage (respiratory tissues) via inhalation or intranasally administration, or parenterally, e.g. via injection.

For ease of exposition, the formulations, compositions, and methods in this section are discussed largely with regard to unmodified iRNA agents. It should be understood, however, that these formulations, compositions, and methods can be practiced with other iRNA agents, e.g., modified iRNA agents, and such practice is within the invention.

A formulated iRNA agent composition can assume a variety of states. In some examples, the composition is at least partially crystalline, uniformly crystalline, and/or anhydrous (e.g., less than 80, 50, 30, 20, or 10% water). In another example, the iRNA agent is in an aqueous phase, e.g., in a solution that includes water, this form being the preferred form for administration via inhalation.

The aqueous phase or the crystalline compositions can be incorporated into a delivery vehicle, e.g., a liposome (particularly for the aqueous phase), or a particle (e.g., a microparticle as can be appropriate for a crystalline composition). Generally, the iRNA agent composition is formulated in a manner that is compatible with the intended method of administration.

An iRNA agent preparation can be formulated in combination with another agent, e.g., another therapeutic agent or an agent that stabilizes an iRNA agent, e.g., a protein that complexes with the iRNA agent to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the iRNA agent preparation includes another iRNA agent, e.g., a second iRNA agent that can mediate RNAi with respect to a second gene. Still other preparations can include at least three, five, ten, twenty, fifty, or a hundred or more different iRNA species. In some embodiments, the agents are directed to the same virus but different target sequences. In another embodiment, each iRNA agents is directed to a different virus. As demonstrated in the Example, more than one virus can be inhibited by co-administering two iRNA agents simultaneously, or at closely time intervals, each one directed to one of the viruses being treated.

Treatment Methods and Routes of Delivery

A composition that includes an iRNA agent of the present invention, e.g., an iRNA agent that targets RSV, can be delivered to a subject by a variety of routes. Exemplary routes include inhalation, intravenous, nasal, or oral delivery. The preferred means of administering the iRNA agents of the present invention is through direct administration to the lungs and nasal passage or systemically through parental administration.

An iRNA agent can be incorporated into pharmaceutical compositions suitable for administration. For example, compositions can include one or more iRNA agents and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including intranasal or intrapulmonary), oral or parenteral. Parenteral administration includes intravenous drip, subcutaneous, intraperitoneal or intramuscular injection.

In general, the delivery of the iRNA agents of the present invention is done to achieve delivery into the subject to the site of infection. The preferred means of achieving this is through either a local administration to the lungs or nasal passage, e.g. into the respiratory tissues via inhalation, nebulization or intranasal administration, or via systemic administration, e.g. parental administration.

Formulations for inhalation or parenteral administration are well known in the art. Such formulation may include sterile aqueous solutions which may also contain buffers, diluents and other suitable additives, an example being PBS or Dextrose 5% in water. For intravenous use, the total concentration of solutes should be controlled to render the preparation isotonic.

The active compounds disclosed herein are preferably administered to the lung(s) or nasal passage of a subject by any suitable means. Active compounds may be administered by administering an aerosol suspension of respirable particles comprised of the active compound or active compounds, which the subject inhales. The active compound can be aerosolized in a variety of forms, such as, but not limited to, dry powder inhalants, metered dose inhalants, or liquid/liquid suspensions. The respirable particles may be liquid or solid. The particles may optionally contain other therapeutic ingredients such as amiloride, benzamil or phenamil, with the selected compound included in an amount effective to inhibit the reabsorption of water from airway mucous secretions, as described in U.S. Pat. No. 4,501,729.

The particulate pharmaceutical composition may optionally be combined with a carrier to aid in dispersion or transport. A suitable carrier such as a sugar (i.e., dextrose, lactose, sucrose, trehalose, mannitol) may be blended with the active compound or compounds in any suitable ratio (e.g., a 1 to 1 ratio by weight).

Particles comprised of the active compound for practicing the present invention should include particles of respirable size, that is, particles of a size sufficiently small to pass through the mouth or nose and larynx upon inhalation and into the bronchi and alveoli of the lungs. In general, particles ranging from about 1 to 10 microns in size (more particularly, less than about 5 microns in size) are respirable. Particles of non-respirable size which are included in the aerosol tend to deposit in the throat and be swallowed, and the quantity of non-respirable particles in the aerosol is preferably minimized. For nasal administration, a particle size in the range of 10-500 microns is preferred to ensure retention in the nasal cavity.

Liquid pharmaceutical compositions of active compound for producing an aerosol may be prepared by combining the active compound with a suitable vehicle, such as sterile pyrogen free water. The hypertonic saline solutions used to carry out the present invention are preferably sterile, pyrogen-free solutions, comprising from one to fifteen percent (by weight) of the physiologically acceptable salt, and more preferably from three to seven percent by weight of the physiologically acceptable salt.

Aerosols of liquid particles comprising the active compound may be produced by any suitable means, such as with a pressure-driven jet nebulizer or an ultrasonic nebulizer. See, e.g., U.S. Pat. No. 4,501,729. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation.

Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water) or a dilute aqueous alcoholic solution, preferably made isotonic, but may be hypertonic with body fluids by the addition of, for example, sodium chloride. Optional additives include preservatives if the formulation is not made sterile, for example, methyl hydroxybenzoate, antioxidants, flavoring agents, volatile oils, buffering agents and surfactants.

Aerosols of solid particles comprising the active compound may likewise be produced with any solid particulate therapeutic aerosol generator. Aerosol generators for administering solid particulate therapeutics to a subject produce particles which are respirable and generate a volume of aerosol containing a predetermined metered dose of a therapeutic at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation.

A second type of illustrative aerosol generator comprises a metered dose inhaler. Metered dose inhalers are pressurized aerosol dispensers, typically containing a suspension or solution formulation of the active ingredient in a liquefied propellant. During use these devices discharge the formulation through a valve adapted to deliver a metered volume, typically from 10 to 200 ul, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol, surfactants, such as oleic acid or sorbitan trioleate, antioxidant and suitable flavoring agents.

Administration can be provided by the subject or by another person, e.g., a caregiver. A caregiver can be any entity involved with providing care to the human: for example, a hospital, hospice, doctor's office, outpatient clinic; a healthcare worker such as a doctor, nurse, or other practitioner; or a spouse or guardian, such as a parent. The medication can be provided in measured doses or in a dispenser which delivers a metered dose.

The term "therapeutically effective amount" is the amount present in the composition that is needed to provide the desired level of drug in the subject to be treated to give the anticipated physiological response. In one embodiment, therapeutically effective amounts of two or more iRNA agents, each one directed to a different respiratory virus, e.g. RSV, are administered concurrently to a subject.

The term "physiologically effective amount" is that amount delivered to a subject to give the desired palliative or curative effect.

The term "pharmaceutically acceptable carrier" means that the carrier can be taken into the lungs with no significant adverse toxicological effects on the lungs.

The term "co-administration" refers to administering to a subject two or more agents, and in particular two or more iRNA agents. The agents can be contained in a single pharmaceutical composition and be administered at the same time, or the agents can be contained in separate formulation and administered serially to a subject. So long as the two agents can be detected in the subject at the same time, the two agents are said to be co-administered.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A preferred group of carbohydrates includes lactose, threhalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

Dosage.

An iRNA agent can be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight, and less than 200 nmol of iRNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmol of iRNA agent per kg of bodyweight. The unit dose, for example, can be administered by an inhaled dose or nebulization or by injection. In one example, dosage ranges of 0.02-25 mg/kg is used.

Delivery of an iRNA agent directly to the lungs or nasal passage can be at a dosage on the order of about 1 mg to about 150 mg/nasal passage.

The dosage can be an amount effective to treat or prevent a disease or disorder.

In one embodiment, the unit dose is administered once a day. In other usage, a unit dose is administered twice the first day and then daily. Alternatively, unit dosing can be less than once a day, e.g., less than every 2, 4, 8 or 30 days. In another embodiment, the unit dose is not administered with a frequency (e.g., not a regular frequency). For example, the unit dose may be administered a single time. Because iRNA agent mediated silencing can persist for several days after administering the iRNA agent composition, in many instances, it is possible to administer the composition with a frequency of less than once per day, or, for some instances, only once for the entire therapeutic regimen.

In one embodiment, a subject is administered an initial dose, and one or more maintenance doses of an iRNA agent, e.g., a double-stranded iRNA agent, or siRNA agent, (e.g., a precursor, e.g., a larger iRNA agent which can be processed into an siRNA agent, or a DNA which encodes an iRNA agent, e.g., a double-stranded iRNA agent, or siRNA agent, or precursor thereof). The maintenance dose or doses are generally lower than the initial dose, e.g., one-half less of the initial dose. A maintenance regimen can include treating the subject with a dose or doses ranging from 0.01 μg to 75 mg/kg of body weight per day, e.g., 70, 60, 50, 40, 30, 20, 10, 5, 2, 1, 0.5, 0.1, 0.05, 0.01, 0.005, 0.001, or 0.0005 mg per kg of bodyweight per day. The maintenance doses are preferably administered no more than once every 5-14 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

In one embodiment, the iRNA agent pharmaceutical composition includes a plurality of iRNA agent species. The iRNA agent species can have sequences that are non-overlapping and non-adjacent with respect to a naturally occurring target sequence, e.g., a target sequence of the RSV gene. In another embodiment, the plurality of iRNA agent species is specific for different naturally occurring target genes. For example, an iRNA agent that targets the P protein gene of RSV can be present in the same pharmaceutical composition as an iRNA agent that targets a different gene, for example the N protein gene. In another embodiment, the iRNA agents are specific for different viruses, e.g. RSV.

The concentration of the iRNA agent composition is an amount sufficient to be effective in treating or preventing a disorder or to regulate a physiological condition in humans. The concentration or amount of iRNA agent administered will depend on the parameters determined for the agent and the method of administration, e.g. nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. It will also be appreciated that the effective dosage of an iRNA agent such as an siRNA agent used for treatment may increase or decrease over the course of a particular treatment. Changes in dosage may result and become apparent from the results of diagnostic assays. For example, the subject can be monitored after administering an iRNA agent composition. Based on information from the monitoring, an additional amount of the iRNA agent composition can be administered.

The invention is further illustrated by the following examples, which should not be construed as further limiting.

EXAMPLES

Designing Antiviral siRNAs Against RSV mRNA siRNA against RSV P, N and L mRNA were synthesized chemically using know procedures. The siRNA sequences and some inhibition cross-subtype activity and IC50 values are listed (Table 1 (a-c)).

In Vitro Assay and Virus Infection

Vero E6 cells were cultured to 80% confluency in DMEM containing 10% heat-inactivated FBS. For siRNA introduction, 4 μl of Transit-TKO was added to 50 μl of serum-free DMEM and incubated at room temperature for 10 minutes. Then, indicated concentration of siRNA was added to media/TKO reagent respectively and incubated at room temperature for 10 minutes. RNA mixture was added to 200 μl of DMEM containing 10% FBS and then to cell monolayer. Cells were incubated at 37° C., 5% $CO_2$ for 6 hours. RNA mixture was removed by gentle washing with 1× Hank's Balanced Salt Solutions (HBSS) and 300 plaque-forming units (pfu) per well of RSV/A2 (MOI=30) was added to wells and adsorbed for 1 hour at 37° C., 5% $CO_2$. Virus was removed and cells were washed with 1×HBSS. Cells were overlaid with 1% methylcellulose in DMEM containing 10% FBS media, and incubated for 6 days at 37° C., 5% $CO_2$. Cells were immunostained for plaques using anti-F protein monoclonal antibody 131-2A.

sIRNA Delivery and Virus Infection In Vivo

Pathogen-free 4 week old female BALB/c mice were purchased from Harlan. Mice were under anesthesia during infection and intranasal instillation (i.n.). Mice were immunized by intranasal instillation with indicated amount of siRNA, either uncomplexed, or complexed with 5 ul Transit TKO. 150 µg of Synagis (monoclonal antibody clone 143-6C, anti-RSV F protein) and Mouse Isotype control (IgG1) were administered intraperitoneal (i.p.) four hours prior to RSV challenge ($10^6$ PFU of RSV/A2). Ten mice per group were used. Animal weights were monitored at days 0, 2, 4, and 6 post-infection. Lungs were harvested at day 6 post-infection, and assayed for RSV by immunostaining plaque assay.

Immunostaining Plaque Assay 24-well plates of Vero E6 cells were cultured to 90% confluency in DMEM containing 10% heat inactivated FBS. Mice lungs were homogenized with hand-held homogenizer in 1 ml sterile Dulbecco's PBS (D-PBS) and 10 fold diluted in serum-free DMEM. Virus containing lung lysate dilutions were plated onto 24 well plates in triplicate and adsorbed for 1 hour at 37° C., 5% $CO_2$. Wells were overlaid with 1% methylcellulose in DMEM containing 10% FBS. Then, plates were incubated for 6 days at 37° C., 5% $CO_2$. After 6 days, overlaid media was removed and cells were fixed in acetone:methanol (60:40) for 15 minutes. Cells were blocked with 5% dry Milk/PBS for 1 hour at 37° C. 1:500 dilution of anti-RSV F protein antibody (131-2A) was added to wells and incubated for 2 hours at 37° C. Cells were washed twice in PBS/0.5% Tween 20. 1:500 dilution of goat anti-mouse IgG-Alkaline Phosphatase was added to wells and incubated for 1 hour at 37° C. Cells were washed twice in PBS/0.5% Tween 20. Reaction was developed using Vector's Alkaline Phosphatase substrate kit II (Vector Black), and counterstained with Hematoxylin. Plaques were visualized and counted using an Olympus Inverted microscope.

Treatment Assay

Mice were challenged with RSV ($10^6$ PFU of RSV/A2) by intranasal instillation at day 0 and treated with 50 ug of indicated siRNA, delivered by intranasal instillation, at the indicated times (day 1-4 post viral challenge). 3-5 mice per group were used and viral titers were measured from lung lysates at day 5 post viral challenge, as previously described.

In Vitro Inhibition of RSV Using iRNA Agents.

iRNA agents provided in Table 1 (a-c) were tested for anti-RSV activity in a plaque formation assay as described above (FIG. 1). Each column (bar) represents an iRNA agent provided in Table 1 (a-c), e.g. column 1 is the first agent in Table 1a, second column is the second agent and so on. Active iRNA agents were identified by the % of virus remaining. Several agents were identified that showed as much as 90% inhibition. The results are summarized in Table 1 (a-c).

In vitro dose response inhibition of RSV using iRNA agents was determined Examples of active agents from Table 1 were tested for anti-RSV activity in a plaque formation assay as described above at four concentrations. A dose dependent response was found with active iRNA agent tested (FIG. 2) and is summarized in Tables 1(a-c).

In vitro inhibition of RSV B subtype using iRNA agents was tested as described above. iRNA agents provided in FIG. 2 were tested for anti-RSV activity against subtype B (FIG. 3). RSV subtype B was inhibited by the iRNA agents tested to varying degrees and is summarized in Table 1(a-c).

In Vivo Inhibition of RSV Using iRNA Agents.

Figure 4:
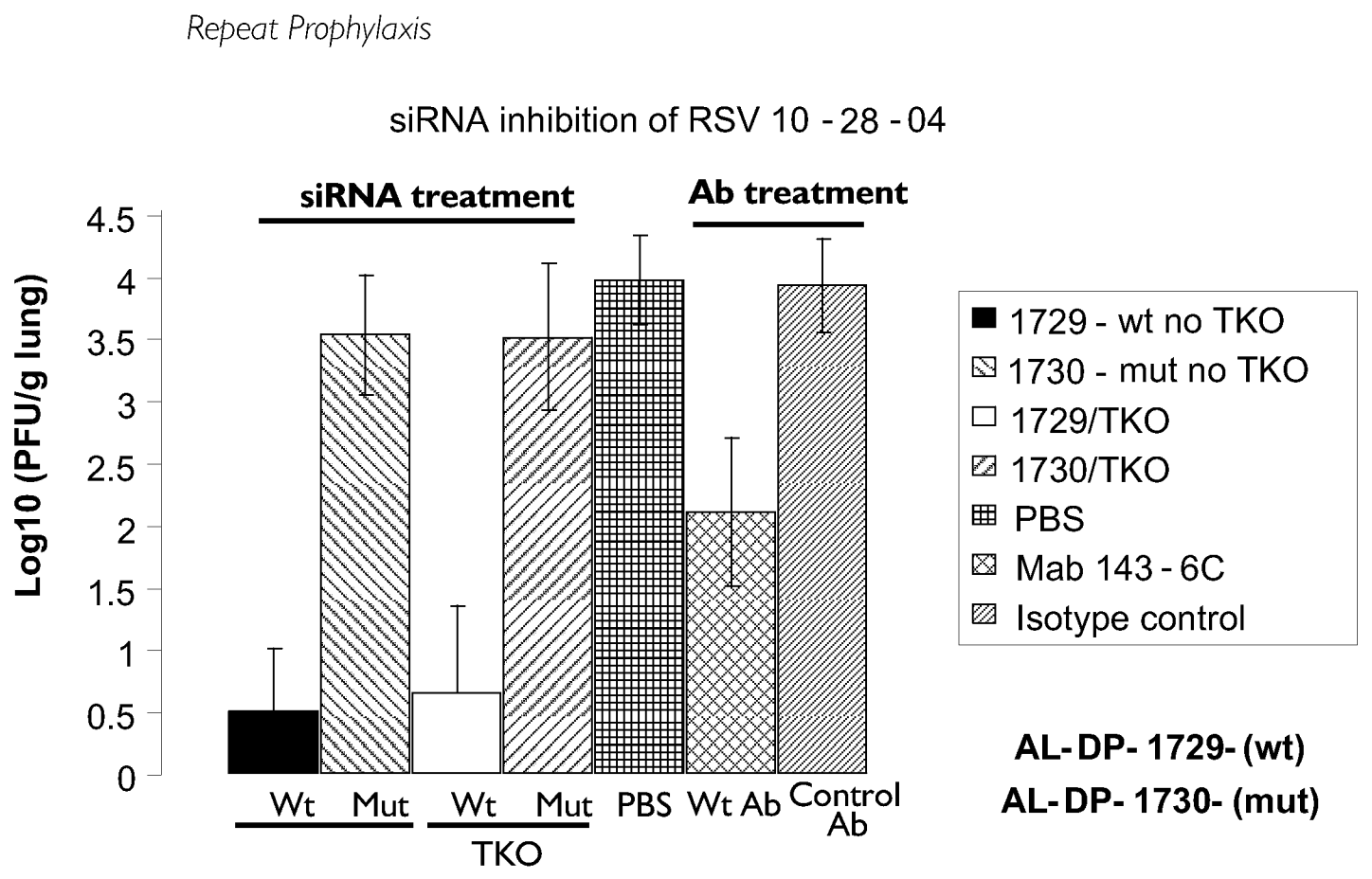

In vivo inhibition of RSV using AL1729 and AL1730 was tested as described above. Agents as described in FIG. 4 were tested for anti-RSV activity in a mouse model. The iRNA agents were effective at reducing viral titers in vivo and more effective than a control antibody (Mab 143-6c, a mouse IgG1 Ab that is approved for RSV treatment).

AL1730 was tested for dose dependent activity using the methods provided above. The agents showed a dose dependent response (FIG. 5).

iRNA agents showing in vitro activity were tested for anti-RSV activity in vivo as outlined above. Several agents showed a reduction in viral titers of >4 logs when given prophylactically (FIG. 6).

iRNA agents showing in vitro and/or in vivo activity were tested for anti-RSV activity in vivo as in the treatment protocol outlined above. Several agents showed a reduction in viral titers of 2-3 logs (FIG. 7) when given 1-2 days following viral infection.

Sequence Analysis of Isolates Across Target Sequence Method:

Growth of Isolates and RNA Isolation:

Clinical isolates from RSV infected patients were obtained from Larry Anderson at the CDC in Atlanta Ga. (4 strains) and John DeVincenzo at the University of Term., Memphis (15 strains). When these were grown in HEp-2, human epithelial cells (ATCC, Cat #CCL-23) cells, it was noted that the 4 isolates from Georgia were slower growing than the 15 strains from Tennessee; hence, these were processed and analyzed separately. The procedure is briefly described as follows:

Vero E6, monkey kidney epithelial cells (ATCC, Cat #CRL-1586) were grown to 95% confluency and infected with a 1/10 dilution of primary isolates. The virus was absorbed for 1 hour at 37° C., then cells were supplemented with D-MEM and incubated at 37° C. On a daily basis, cells were monitored for cytopathic effect (CPE) by light microscopy. At 90% CPE, the cells were harvested by scraping and pelleted by centrifugation at 3000 rpm for 10 minutes. RNA preparations were performed by standard procedures according to manufacturer's protocol.

Amplification of RSV N Gene:

Viral RNAs were collected post-infection and used as templates in PCR reactions, using primers that hybridize upstream and downstream of the ALDP-2017 target site to amplify an ~450 bp fragment. Total RNA was denatured at 65° C. for 5 minutes in the presence of forward and reverse RSV N gene primers, stored on ice, and then reverse-transcribed with Superscript 111 (Invitrogen) for 60 minutes at 55° C. and for 15 minutes at 70° C. PCR products were analyzed by gel electrophoresis on a 1% agarose gel and purified by standard protocols.

Results:

Sequence analysis of the first 15 isolates confirmed that the target site for ALDP-2017 was completely conserved across every strain. Importantly, this conservation was maintained across the diverse populations, which included isolates from both RSV A and B subtypes. Interestingly, when the 4 slower-growing isolates were analyzed, we observed that one of the 4 (LAP6824) had a single base mutation in the ALDP-2017 recognition site. This mutation changed the coding sequence at position 13 of the RSV N gene in this isolate from an A to a G.

Conclusions:

From 19 patient isolates, the sequence of the RSV N gene at the target site for ALDP-2017 has been determined. In 18 of 19 cases (95%), the recognition element for ALDP-2017 is 100% conserved. In one of the isolates, there is a single base alteration changing the nucleotide at position 13 from an A to a G within the RSV N gene. This alteration creates a single G:U wobble between the antisense strand of ALDP-2017 and the target sequence. Based on an understanding of the hybridization potential of such a G:U wobble, it is predicted that ALDP-2017 will be effective in silencing the RSV N gene in this isolate.

Silencing Data on Isolates

Methods:

Vero E6 cells were cultured to 80% confluency in DMEM containing 10% heat-inactivated FBS. For siRNA introduction, 4 µl of Transit-TKO was added to 50 µl of serum-free DMEM and incubated at room temperature for 10 minutes. Then, indicated concentration of siRNA was added to media/TKO reagent respectively and incubated at room temperature for 10 minutes. RNA mixture was added to 200 µl of DMEM containing 10% FBS and then to cell monolayer. Cells were incubated at 37° C., 5% $CO_2$ for 6 hours. RNA mixture was removed by gentle washing with 1× Hank's Balanced Salt Solutions (HBSS) and 300 plaque-forming units (pfu) per well of RSV/A2 (MOI=30) was added to wells and adsorbed for 1 hour at 37° C., 5% $CO_2$. Virus was removed and cells were washed with 1×HBSS. Cells were overlaid with 1% methylcellulose in DMEM containing 10% FBS media, and incubated for 6 days at 37° C., 5% $CO_2$. Cells were immunostained for plaques using anti-F protein monoclonal antibody 131-2A.

Results:

Silencing was seen for all isolates (Table 2)

TABLE 2

| Isolate name | 2017 % plaques remaining | 2153 % plaques remaining |
|---|---|---|
| RSV/A2 | 4.49 | 80.34 |
| RSV/96 | 5.36 | 87.50 |
| RSV/87 | 10.20 | 79.59 |
| RSV/110 | 5.41 | 81.08 |
| RSV/37 | 4.80 | 89.60 |
| RSV/67 | 2.22 | 91.67 |
| RSV/121 | 6.25 | 82.50 |
| RSV/31 | 4.03 | 96.77 |
| RSV/38 | 2.00 | 92.67 |
| RSV/98 | 5.13 | 91.03 |
| RSV/124 | 3.74 | 90.37 |
| RSV/95 | 7.32 | 64.02 |
| RSV/32 | 5.45 | 92.73 |
| RSV/91 | 8.42 | 95.79 |
| RSV/110 | 12.07 | 94.83 |
| RSV/54 | 1.90 | 89.87 |
| RSV/53 | 7.41 | 94.07 |
| RSV/33 | 7.69 | 95.19 |

Conclusion:

All clinical isolates tested were specifically inhibited by siRNA 2017 by greater than 85%. No isolates were significantly inhibited the mismatch control siRNA 2153.

Silencing in Plasmid Based Assay

Method:

A 24-well plate is seeded with HeLa S6 cells and grown to 80% confluence. For each well, mix 1 ug of RSV N-V5 plasmid with siRNA (at indicated concentration), in 50 ul OPTIMEM and add to Lipofectamine 2000 (Invitrogen)-Optimem mixture prepared according to manufacturer's instructions, and let sit 20 minutes at r.t. to form complex. Add complex to cells and incubate 37° C. overnight. Remove the media, wash the cells with PBS and lyse with 50 ul Lysis buffer (RIPA buffer (50 mM Tris-HCl pH 8.0, 150 mM NaCl, 1 mM EDTA, 0.5% Na deoxycholate, 1% NP-40, 0.05% SDS) for 1-2 min. Lysates are analysed using Inhibition is quantified by measuring the level of RSV protein in cell lysates, detected by western blotting with an anti-V5 antibody Results:

Transient plasmid expression was shown to be an effective assay for RNAi agents (Table 3).

TABLE 3

| | | | Protein % | Activity % |
|---|---|---|---|---|
| 1 | ALDP2017 | 10 nM | 0 | 100 |
| 2 | | 1 nM | 0 | 100 |
| 3 | | 100 pM | 0 | 100 |
| 4 | | 10 pM | 11.78 | 88.22 |
| 5 | | 1 pM | 70.63 | 29.37 |
| 6 | | 100 fM | 72.7 | 27.3 |
| 7 | Control | PBS | 100 | 0 |
| 8 | 2153 | 10 nM | 94.54 | 4.5 |

Conclusions:

siRNA 2017 specifically and dose dependently inhibits the production of RSV N protein when transiently cotranfected with plasmid expressing the RSV N gene. Inhibition is not observed with mismatch control siRNA 2153.

Silencing of RSV Via Aerosol Delivery of siRNA

Method:

A 2 mg/ml solution of ALDP-1729 or ALDP-1730 is delivered via nebulization using an aerosol device for a total of 60 sec. Viral is prepared from lung as described above and measured by an ELISA instead of a plaque assay. The ELISA measures the concentration of the RSV N protein in cells infected with virus obtained from mouse lung lysates.

ELISA

Lung lystate is diluted 1:1 with carbonate-bicarbonate buffer ($NaHCO_3$ pH 9.6) to a working concentration of 6-10 ng/100 µL, added to each test well and incubated at 37° C. for 1 hour or overnight at 4° C. Wells washed 3× with PBS/0.5% Tween 20 then blocked with 5% dry milk/PBS for 1 hour at 37° C. or overnight at 4° C. Primary antibody (F protein positive control=clone 131-2A; G protein positive control=130-2G; negative control=normal IgG1, (BD Pharmingen, cat. #553454, test sera, or hybridoma supernatant) is added to wells at 1:1000 and incubated at 37° C. for 1 hour or overnight at 4° C. Wells washed 3× with PBS/0.5% Tween 20. Secondary antibody (Goat Anti-mouse IgG (H+L) whole molecule-alkaline phosphatase conjugated) diluted 1:1000 to wells (100 µl/well) is added and incubated at 37° C. for 1 hour or overnight at 4° C. Wash 3× with PBS/0.5% Tween 20 then add Npp (Sigmafast) substrate Sigma Aldrich N2770 accordingly to manufacturers instructions. Add 200 µl of substrate/well and incubate for 10-15. Measure absorbance at OD 405/495.

Figure 8A:
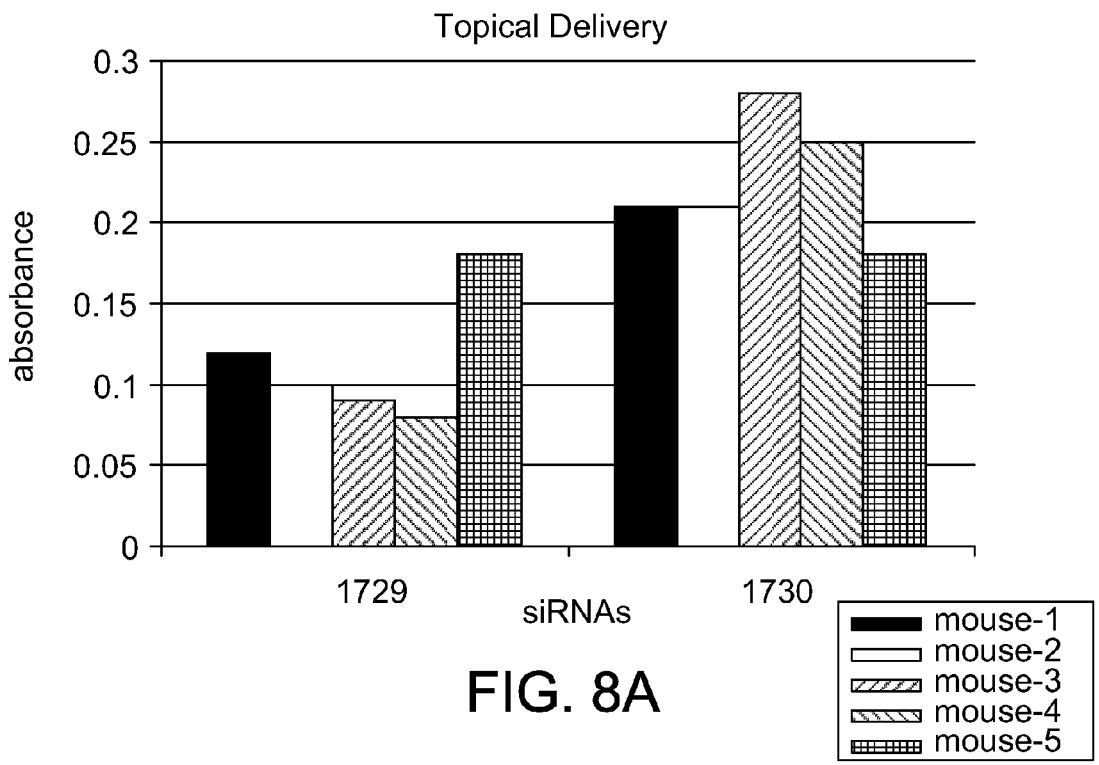
FIGS. 8A and 8B: In vivo inhibition of RSV using iRNA agents delivered via aerosol. iRNA agents described in the Figure were tested for anti-RSV activity in vivo as described in the Example.
Figure 8B:
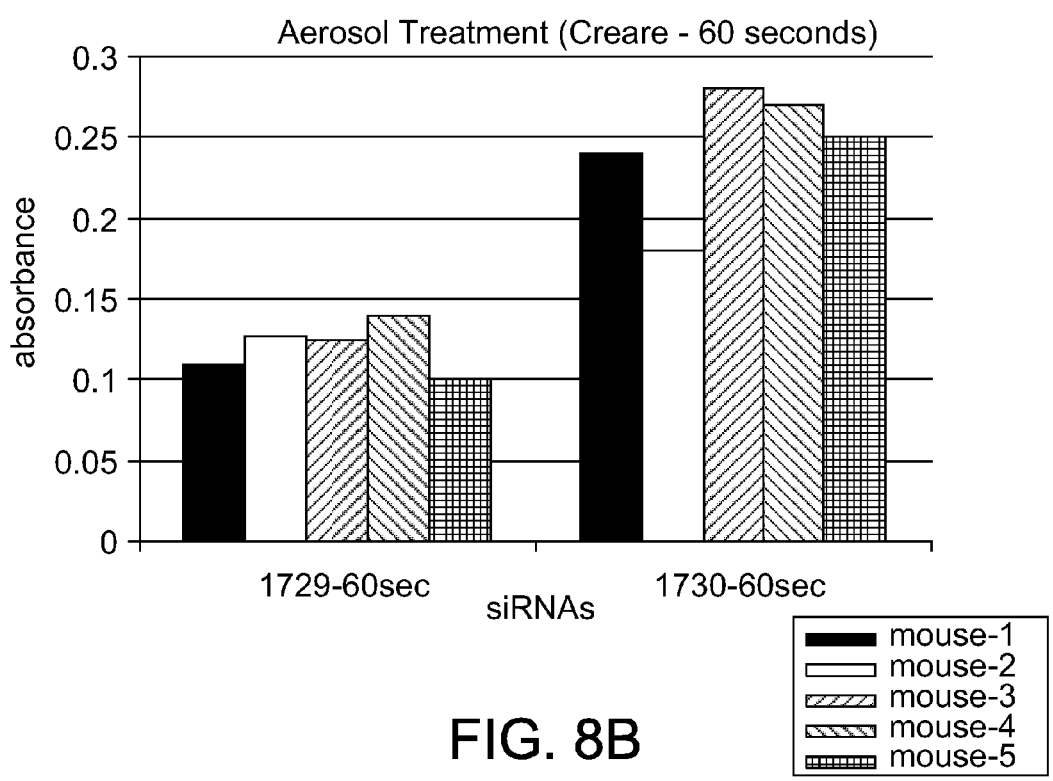

Conclusion:

Delivery of RSV specific siRNA decreases the levels of RSV N protein in mouse lungs as compared to the mismatch control siRNA (FIG. 8a-b).

In Vivo Inhibition at Day-3-Prophylaxis

Method:

In vivo prophylaxis was tested using the in vivo method described above except that the siRNA is delivered at different times prior to infection with RSV from 3 days before to 4 hrs before.

Figure 9:
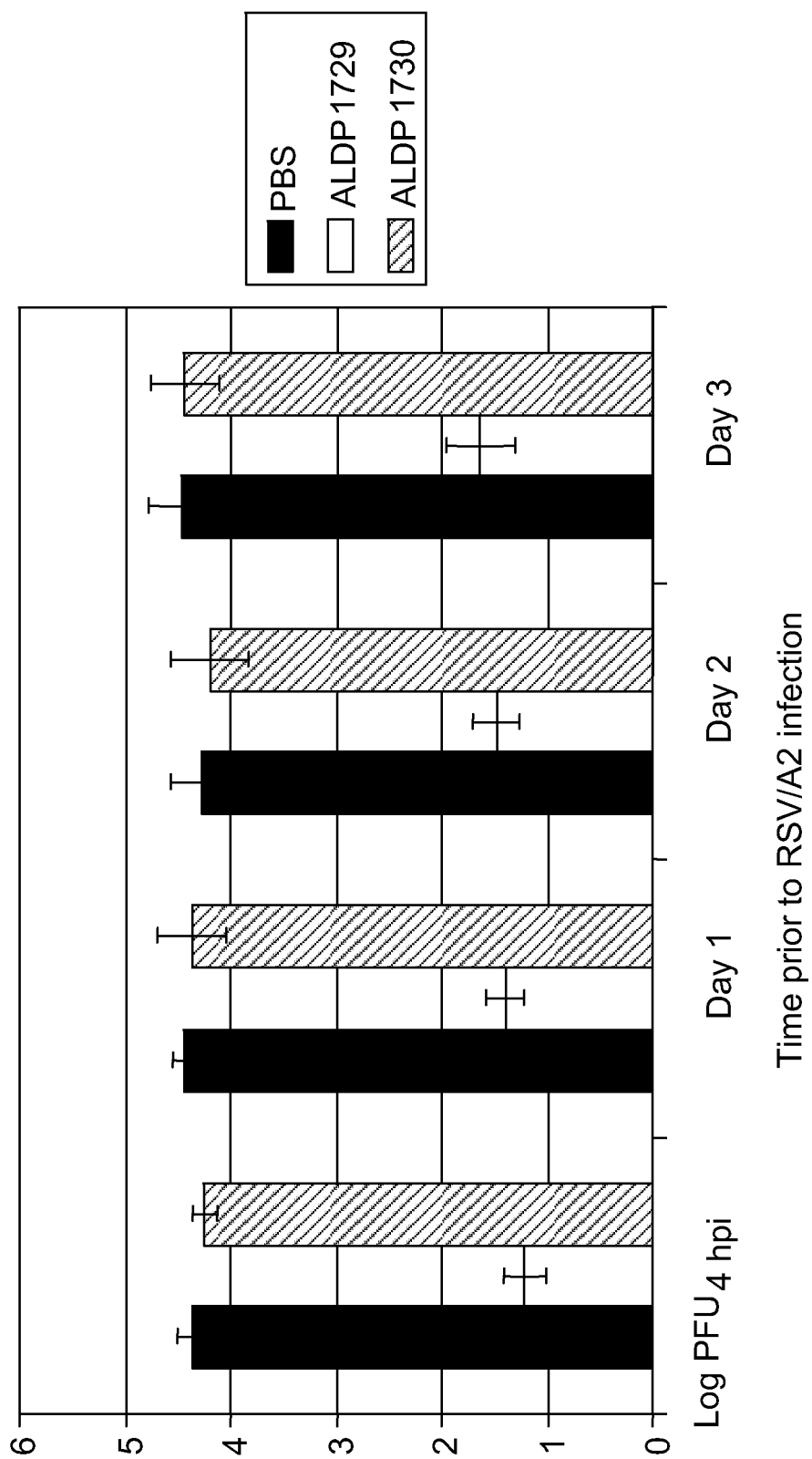
FIG. 9: In vivo protection against RSV infection using iRNA agents. iRNA agents described in the Figure were tested prior to RSV challenge to test for protective activity.

Results:

siRNA delivered intranasally up to 3 days prior to viral challenge show significant silencing in vivo (FIG. 9).

Nebulization of AL-DP 2017 with Pari eFlow® Device

Droplet Size and Analytical Integrity

A 75 mg/ml solution of AL-DP 2017 (in 2 mls of PBS) was filled into the Pari eFlow® electronic device and run until nebulization was completed and all aerosol was collected and allowed to condense in a polypropylene tube. Aliquots of material post nebulization were analyzed to determine geometric droplet size distribution by laser diffraction (Malvern MasterSizerX) under standard conditions. Aliquots of material pre and post nebulization were analyzed to determine analytical integrity by a stability indicating anion exchange HPLC method.

Results:

Aerosolized AL-DP 2017 had a Mass Median Diameter (MMD) of 3.1 m, a Geometric Standard Deviation (GSD) of 1.6 and a total respirable fraction of 85% (ie, % particles<5 m) confirming that a 75 mg/ml solution could be aerosolized to yield respirable material with appropriate particle size. Comparison to control samples of AL-DP 2017 formulation which were not nebulized showed matching chromatograms, demonstrating that the oligonucleotide can be nebulized by eFlow® without degradation.

Biological Activity:

A 25 mg/ml solution of AL-DP 2017 (in 1 mls of PBS) was prepared, 100 µl was removed (pre-nebulization aliquot) prior to nebulization with the Pari eFlow® electronic device, and 500 ul of the nebulized solution was collected after condensing by passage over an ice bath into a chilled 50 ml conical tube (post-nebulization aliquot). Serial dilutions of both aliquots were tested in our in vitro transfection/infection plaque assay as previously described with the exception that siRNA is complexed with lipofetamine-2000.

Figure 10:
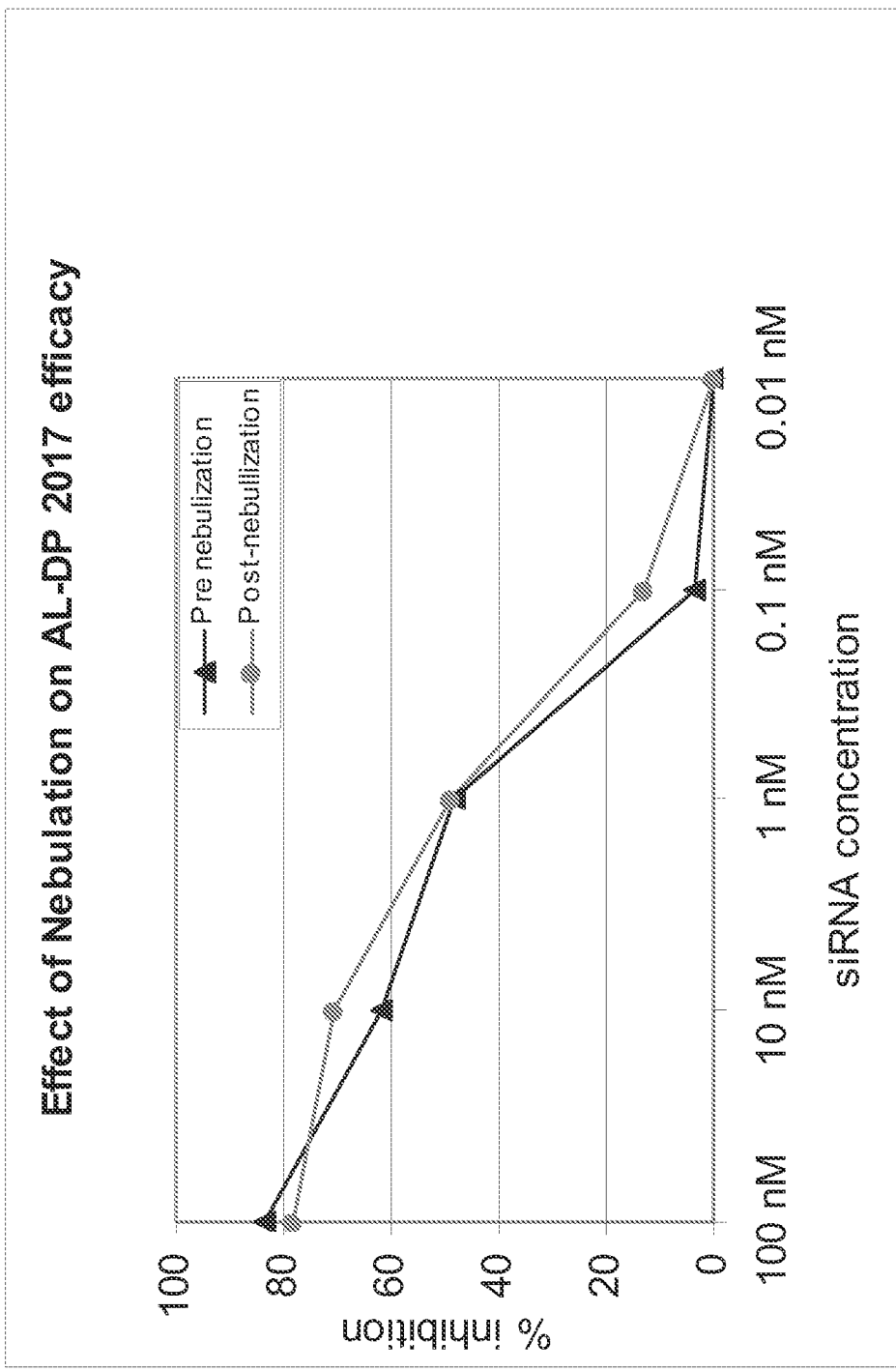
FIG. 10: In vitro activity of nebulized iRNA agents. iRNA agents as described were nebulized and shown to retain activity in an in vitro assay of RSV infection.

Results:

siRNA pre and post nebulization efficiently inhibited RSV viral replication in a Vero cell plaque assay. The degree of inhibition was almost identical between the two samples and showed a dose response leading to >80% silencing at the highest siRNA concentrations confirming that nebulized AL-DP 2017 maintains biological activity (FIG. 10).

TABLE 1 (a-c)

siRNA sequences

Table 1a. RSV L gene

| Actual start | Whitehead Start Pos | Sense | SEQ ID NO: | Antisense | SEQ ID NO: | AL-DP # | % inh RSV A2 (5 nM) | % inh RSV A2 500 pM | % inh RSV A2 50 pM | % inh RSV A2 5 pM | % inh RSV B (5 nM) |
|---|---|---|---|---|---|---|---|---|---|---|---|
| 3 | 1 | GGAUCCCAUUAUU AAUGGAdTdT | 1 | UCCAUUAAUAUG GGAUCCdTdT | 2 | AL-DP-2024 | 92 | | | | |
| 4 | 2 | GAUCCCAUUAUUA AUGGAAdTdT | 3 | UUCCAUUAAUAAU GGGAUCdTdT | 4 | AL-DP-2026 | 82 | | | | |
| 49 | 47 | AGUUAUUUAAAAG GUGUUAdTdT | 5 | UAACACCUUUUAA AUAACUdTdT | 6 | AL-DP-2116 | | | | | |
| 50 | 48 | GUUAUUUAAAAGG UGUUAUdTdT | 7 | AUAACACCUUUUA AAUAACdTdT | 8 | AL-DP-2117 | | | | | |
| 53 | 51 | AUUUAAAAGGUGU UAUCUCdTdT | 9 | GAGAUAACACCUU UUAAAUdTdT | 10 | AL-DP-2118 | | | | | |
| 55 | 53 | UUAAAAGGUGUUA UCUCUUdTdT | 11 | AAGAGAUAACACC UUUUAAdTdT | 12 | AL-DP-2119 | | | | | |
| 156 | 154 | AAGUCCACUACUA GAGCAUGdTdT | 13 | AUGCUCUAGUAGU GGACUUdTdT | 14 | AL-DP-2027 | 86 | | | | |
| 157 | 155 | AGUCCACUACUAG AGCAUAUdTdT | 15 | UAUGCUCUAGUAG UGGACUdTdT | 16 | AL-DP-2028 | 90 | | | | |
| 158 | 156 | GUCCACUACUAGA GCAUAUGdTdT | 17 | AUAUGCUCUAGUA GUGGACdTdT | 18 | AL-DP-2029 | 89 | | | | |
| 159 | 157 | UCCACUACUAGAG CAUAUGAdTdT | 19 | CAUAUGCUCUAGU AGUGGAdTdT | 20 | AL-DP-2030 | 86 | | | | |
| 341 | 339 | GAAGAGCUAUAGA AAUAAGdTdT | 21 | CUUAUUUCUAUAG CUCUUCdTdT | 22 | AL-DP-2120 | | | | | |
| 344 | 342 | GAGCUAUAGAAAU AAGUGAdTdT | 23 | UCACUUAUUUCUA UAGCUCdTdT | 24 | AL-DP-2121 | | | | | |
| 347 | 345 | CUAUAGAAAUAAG UGAUGUdTdT | 25 | ACAUCACUUAUUU CUAUAGdTdT | 26 | AL-DP-2031 | 15 | | | | |
| 554 | 552 | UCAAAACAACACU CUUGAAdTdT | 27 | UUCAAGAGUGUUG UUUUGAdTdT | 28 | AL-DP-2122 | | | | | |

TABLE 1 (a-c)-continued

| | siRNA sequences | | | |
|---|---|---|---|---|
| 1004 | UAGAGGGAUUUAUUAUGUCdTdT | 29 | GACAUAUAAAUCCCUCUAdTdT | 30 | AL-DP-2123 | |
| 1408 | AUAAAAGGGUUUGUAAAUAdTdT | 31 | UAUUUACAAACCCUUUUAUdTdT | 32 | AL-DP-2124 | |
| 1867 | CUCAGUUAGGUAGAAUGUdTdT | 33 | ACAUUCUACCACUGAGdTdT | 34 | AL-DP-2032 | 90 |
| 1868 | UCAGUGUAGGUAGAAUGUUdTdT | 35 | AACAUUCUACCUACACUGAdTdT | 36 | AL-DP-2033 | 84 |
| 1869 | CAGUGUAGGUAGAAUGUUUdTdT | 37 | AAACAUUCUACCUACACUGdTdT | 38 | AL-DP-2034 | 86 |
| 1870 | AGUGUAGGUAGAAUGUUUGdTdT | 39 | CAAACAUUCUACCUACACUdTdT | 40 | AL-DP-2112 | |
| 1871 | GUGUAGGUAGAAUGUUUGCdTdT | 41 | GCAAACAUUCUACCUACACdTdT | 42 | AL-DP-2113 | 89 |
| 1978 | ACAAGAUAUGGUGAUCUAGdTdT | 43 | CUAGAUCACCAUAUCUUGUdTdT | 44 | AL-DP-2035 | 87 |
| 2104 | AGCAAAUUCAAUCAAGCAUdTdT | 45 | AUGCUUGAUUGAAUUUGCUdTdT | 46 | AL-DP-2036 | 91 |
| 2105 | GCAAAUUCAAUCAAGCAUUdTdT | 47 | AAUGCUUGAUUGAAUUUGCdTdT | 48 | AL-DP-2037 | 11 |
| 2290 | GAUGAACAAAGUGGAUUAUdTdT | 49 | AUAAUCCACUUUGUUCAUCdTdT | 50 | AL-DP-2038 | |
| 2384 | UAAUAUCUCUCAAAGGGAAAUdTdT | 51 | UUCCCUUUGAGAGAUAUUAdTdT | 52 | AL-DP-2125 | |
| 2386 | AUAUCUCUCAAAGGGAAUAUdTdT | 53 | AUUCCCUUUGAGAGAUAUdTdT | 54 | AL-DP-2126 | |
| 2387 | UAUCUCUCAAAGGGAAAUUdTdT | 55 | AAUUCCCUUUGAGAGAUAdTdT | 56 | AL-DP-2127 | |
| 2485 | CAUGCUCAAGCAGAUUAUUdTdT | 57 | AAUAAUCUGCUUGAGCAUGdTdT | 58 | AL-DP-2039 | 87 |
| 2487 | UGCUCAAGCAGAUUAUUGUdTdT | 59 | CAAAUAAUCUGCUUGAGCAdTdT | 60 | AL-DP-2040 | 88 |
| 2505 | UAGCAUUAAAUAGCCUUAAdTdT | 61 | UUAAGGCUAUUUAAUGCUAdTdT | 62 | AL-DP-2041 | 96 |
| 2507 | | | | | | 76 | 73 | 69 | 94 |

TABLE 1 (a-c)-continued

| | | siRNA sequences | | | | | | | | |
|---|---|---|---|---|---|---|---|---|---|---|
| 2508 | 2506 | AGCAUUAAAUAGC CUUAAAdTdT | 63 | UUUAAGGCUAUUU AAUGCUdTdT | 64 | AL-DP-2114 | 96 | 98 | 97 | 97 | 90 |
| 2509 | 2507 | GCAUUAAAUAGCC UUAAAUdTdT | 65 | AUUUAAGGCUAUU UAAUGCdTdT | 66 | AL-DP-2042 | 97 | 86 | 79 | 75 | 94 |
| 2510 | 2508 | CAUUAAAUAGCCU UAAAUUdTdT | 67 | AAUUUAAGGCUAU UUAAUUdTdT | 68 | AL-DP-2043 | 97 | 79 | 72 | 67 | 84 |
| 2765 | 2763 | UAUUAUGCAGUUU AAUAUUdTdT | 69 | AAUAUUAAACUGC AUAAUAdTdT | 70 | AL-DP-2044 | | | | | |
| 2767 | 2765 | UUAUGCAGUUUAA UAUUUAdTdT | 71 | UAAAUAUUAAACU GCAUAAdTdT | 72 | AL-DP-2045 | 15 | | | | |
| 3283 | 3281 | AAAAGUGCACAAC AUAUAAdTdT | 73 | UAUAAUGUGUUGC ACUUUUdTdT | 74 | AL-DP-2128 | | | | | |
| 3284 | 3282 | AAAGUGCACAACA UUAUACdTdT | 75 | GUAUAAUGUGUUG CACUUUdTdT | 76 | AL-DP-2046 | 94 | 94 | 91 | 91 | 93 |
| 3338 | 3336 | AUAUAGAACCUAC AUAUCCdTdT | 77 | GGAUAUGUAGGUU CUAUAUdTdT | 78 | AL-DP-2047 | 87 | | | | |
| 3339 | 3337 | UAUAGAACCUACA UAUCCUdTdT | 79 | AGGAUAUGUAGGU UCUAUAdTdT | 80 | AL-DP-2048 | 84 | | | | |
| 3365 | 3363 | UAAGAGUUGUUUA UGAAAGdTdT | 81 | CUUUCAUAAACAA CUCUUAdTdT | 82 | AL-DP-2129 | 24 | | | | |
| 4021 | 4019 | ACAGUCAGUAGUA GACCAUGdTdT | 83 | AUGGUCUACUACU GACUGUdTdT | 84 | AL-DP-2049 | 15 | | | | |
| 4022 | 4020 | CAGUCAGUAGUAG ACCAUGdTdT | 85 | CAUGGUCUACUAC UGACUGdTdT | 86 | AL-DP-2050 | 87 | | | | |
| 4023 | 4021 | AGUCAGUAGUAGA CCAUGUdTdT | 87 | ACAUGGUCUACUA CUGACUdTdT | 88 | AL-DP-2051 | | | | | |
| 4024 | 4022 | GUCAGUAGUAGAC CAUGUGdTdT | 89 | CACAUGGUCUACU ACUGACdTdT | 90 | AL-DP-2052 | 96 | 84 | 76 | 69 | 87 |
| 4025 | 4023 | UCAGUAGUAGACC AUGUGAdTdT | 91 | UCACAUGGUCUAC UACUGAdTdT | 92 | AL-DP-2053 | 92 | 84 | 79 | 76 | 74 |
| 4037 | 4035 | CAUGUGAAUUCCC UGCAUGdTdT | 93 | CAUGCAGGGAAUU CACAUGdTdT | 94 | AL-DP-2054 | 97 | 79 | 78 | 69 | 96 |
| 4038 | 4036 | AUGUGAAUUCCCU GCAUGAdTdT | 95 | UGAUGCAGGGAAU UCACAUdTdT | 96 | AL-DP-2055 | 88 | | | | |

TABLE 1 (a-c)-continued

| | siRNA sequences | | | | | | | | |
|---|---|---|---|---|---|---|---|---|---|
| 4039 | 97 | UGUGAAUUCCCUG CAUCAAdTdT | 98 | UUGAUGCAGGGAA UUCACAdTdT | AL-DP-2056 | 16 | | | |
| 4040 | 99 | GUGAAUCCCUGC AUCAUdTdT | 100 | AUUGAUGCAGGGA AUCAUdTdT | AL-DP-2115 | | | | |
| 4043 | 101 | AAUUCCCUGCAUC AAUACCdTdT | 102 | GGUAUGAUGCAG GGAAUUdTdT | AL-DP-2057 | 94 | 91 | 86 | 79 | 69 |
| 4051 | 103 | GCAUCAAUACCAG CUUAUAdTdT | 104 | UAUAAGCUGGUAU UGAUGCdTdT | AL-DP-2058 | 86 | | | |
| 4052 | 105 | CAUCAAUACCAGC UUAUAGdTdT | 106 | CUAUAAGCUGGUA UUGAUGdTdT | AL-DP-2059 | 91 | | | |
| 4057 | 107 | AUACCAGCUUAUA GAACAAdTdT | 108 | UUGUUCUAUAAGC UGGUAUdTdT | AL-DP-2060 | 92 | | | |
| 4058 | 109 | UACCAGCUUAUAG AACAACdTdT | 110 | GUUGUUCUAUAAG CUGGUAdTdT | AL-DP-2061 | 88 | | | |
| 4059 | 111 | ACCAGCUUAUAGA ACAACAdTdT | 112 | UGUGUUCUAUAA GCUGGUdTdT | AL-DP-2062 | 95 | 79 | 78 | 72 | 94 |
| 4060 | 113 | CCAGCUUAUAGAA CAACAAdTdT | 114 | UUGUUGUUCUAUA AGCUGGdTdT | AL-DP-2063 | 90 | | | |
| 4061 | 115 | CAGCUUAUAGAAC AACAAAdTdT | 116 | UUUGUUGUUCUAU AAGCUGdTdT | AL-DP-2064 | 94 | 86 | 76 | 67 | 83 |
| 4067 | 117 | AUAGAACAACAAA UAUCAUdTdT | 118 | UGAUAAUUGUGUU UUCUAUdTdT | AL-DP-2065 | 91 | | | |
| 4112 | 119 | UAUUAACAGAAAA GUAUGGdTdT | 120 | CCAUACUUUUCUG UUAAUAdTdT | AL-DP-2130 | | | | |
| 4251 | 121 | UGAGAUACAUUUG AUGAAAdTdT | 122 | UUUCAUCAAAUGU AUCUCAdTdT | AL-DP-2066 | 86 | | | |
| 4252 | 123 | GAGAUACAUUUG AUGAAAUdTdT | 124 | GUUUCAUCAAAUG UAUCUCdTdT | AL-DP-2067 | 92 | | | |
| 4254 | 125 | GAUACAUUUGAU GAAACUdTdT | 126 | AGGUUUCAUCAAA UGUAUCdTdT | AL-DP-2068 | 93 | | | |
| 4255 | 127 | AUACAUUUGAUGA AACCUdTdT | 128 | GAGGUUUCAUCAA AUGUAUdTdT | AL-DP-2069 | 89 | | | |
| 4256 | 129 | UACAUUGAUGA AACCUCCdTdT | 130 | GGAGGUUUCAUCA AAUGUAdTdT | AL-DP-2074 | | | | |

TABLE 1 (a-c)-continued siRNA sequences

| | | | | | |
|---|---|---|---|---|---|
| 4313 | AAGUGAUACAAA AACAGCAdTdT | 131 | UGCUGUUUUGUA UCACUUdTdT | 132 | AL-DP-2131 |
| 4314 | AGUGAUACAAAA ACAGCAUdTdT | 133 | AUGCUGUUUUGU AUCACUdTdT | 134 | AL-DP-2132 |
| 4316 | UGAUACAAAAAC AGCAUAUdTdT | 135 | AUAUGCUGUUUU GUAUCAdTdT | 136 | AL-DP-2133 |
| 4471 | UUUAAGUACUAA UUUAGCUdTdT | 137 | AGCUAAAUUAGUA CUUAAAdTdT | 138 | AL-DP-2075 |
| 4472 | UUAAGUACUAAU UUAGCUGdTdT | 139 | CAGCUAAAUUAGU ACUUAAdTdT | 140 | AL-DP-2076 |
| 4473 | UAAGUACUAAUU UAGCUGGdTdT | 141 | CCAGCUAAAUUAG UACUUAdTdT | 142 | AL-DP-2077 |
| 4474 | AAGUACUAAUUU AGCUGGAdTdT | 143 | UCCAGCUAAAUUA GUACUUdTdT | 144 | AL-DP-2078 |
| 4475 | AGUACUAAUUUA GCUGGACdTdT | 145 | GUCCAGCUAAAUU AGUACUdTdT | 146 | AL-DP-2079 |
| 4476 | GUACUAAUUUAG CUGGACAdTdT | 147 | UGUCCAGCUAAAU UAGUACdTdT | 148 | AL-DP-2080 |
| 4478 | ACUAAUUUAGCU GGACAUUdTdT | 149 | AAUGUCCAGCUAA AUUAGUdTdT | 150 | AL-DP-2081 |
| 4481 | AAUUUAGCUGGA CAUUGGAdTdT | 151 | UCCAAUGUCCAGC UAAAUUdTdT | 152 | AL-DP-2082 |
| 4482 | AUUUAGCUGGAC AUUGGAUdTdT | 153 | AUCCAAUGUCCAG CUAAAUdTdT | 154 | AL-DP-2083 |
| 4484 | UUAGCUGGACAU UGGAUUCdTdT | 155 | GAAUCCAAUGUCC AGCUAAdTdT | 156 | AL-DP-2084 |
| 4537 | UUUUGAAAAAGA UUGGGGAdTdT | 157 | UCCCCAAUCUUUU UCAAAAdTdT | 158 | AL-DP-2134 |
| 4538 | UUUGAAAAAGAU UGGGGAGdTdT | 159 | CUCCCCAAUCUUU UUCAAAdTdT | 160 | AL-DP-2135 |
| 4540 | UGAAAAGAUUG GGGAGGdTdT | 161 | CUCUCCCCAAUCU UUUUCAdTdT | 162 | AL-DP-2136 |
| 4541 | GAAAAAGAUUGG GGAGGGdTdT | 163 | CCCUCCCCAAUC UUUUUCdTdT | 164 | AL-DP-2137 |

TABLE 1 (a-c)-continued

| | | siRNA sequences | | |
|---|---|---|---|---|
| 4671 | UAUGAACACUUC AGAUCUUdTdT | 165 | AAGAUCUGAAGUG UUCAUAdTdT | 166 | AL-DP-2085 |
| 4672 | AUGAACACUUCA GAUCUUCdTdT | 167 | GAAGAUCUGAAGU GUUCAUdTdT | 168 | AL-DP-2086 |
| 4867 | UGCCCUUGGGUU GUUAACAdTdT | 169 | UGUUAACAACCCA AGGGCAdTdT | 170 | AL-DP-2087 |
| 4868 | GCCCUUGGGUUG UUAACAUdTdT | 171 | AUGUUAACAACCC AAGGGCdTdT | 172 | AL-DP-2088 |
| 5542 | UAUAGCAUUCAU AGGUGAAdTdT | 173 | UUCACCUAUGAAU GCUAUAdTdT | 174 | AL-DP-2089 |
| 5543 | AUAGCAUUCAUA GGUGAAGdTdT | 175 | CUUCACCUAUGAA UGCUAUdTdT | 176 | AL-DP-2090 |
| 5544 | UAGCAUUCAUAG GUGAAGGdTdT | 177 | CCUUCACCUAUGA AUGCUAdTdT | 178 | AL-DP-2091 |
| 5548 | AUUCAUAGGUGA AGGAGCAdTdT | 179 | UGCUCCUUCACCU AUGAAUdTdT | 180 | AL-DP-2092 |
| 5638 | UUGCAAUGAUCA UAGUUUAdTdT | 181 | UAAACUAUGAUCA UUGCAAdTdT | 182 | AL-DP-2093 |
| 5639 | UGCAAUGAUCAU AGUUUACdTdT | 183 | GUAAACUAUGAUC AUUGCAdTdT | 184 | AL-DP-2094 |
| 5640 | GCAAUGAUCAUA GUUUACCdTdT | 185 | GGUAAACUAUGAU CAUUGCdTdT | 186 | AL-DP-2095 |
| 5641 | CAAUGAUCAUAG UUUACCUdTdT | 187 | AGGUAAACUAUGA UCAUUGdTdT | 188 | AL-DP-2096 |
| 5642 | AAUGAUCAUAGU UUACCUAdTdT | 189 | UAGGUAAACUAUG AUCAUUdTdT | 190 | AL-DP-2097 |
| 5643 | AUGAUCAUAGUU UACCUAUdTdT | 191 | AUAGGUAAACUAU GAUCAUdTdT | 192 | AL-DP-2098 |
| 5645 | GAUCAUAGUUUA CCUAUUGdTdT | 193 | CAAUAGGUAAACU AUGAUCdTdT | 194 | AL-DP-2138 |
| 5646 | AUCAUAGUUUAC CUAUUGAdTdT | 195 | UCAAUAGGUAAAC UAUGAUdTdT | 196 | AL-DP-2139 |
| 5647 | UCAUAGUUUACC UAUUGAGdTdT | 197 | CUCAAUAGGUAAA CUAUGAdTdT | 198 | AL-DP-2140 |

TABLE 1 (a-c)-continued

| | | siRNA sequences | | | |
|---|---|---|---|---|---|
| 5650 | 5648 | CAUAGUUUACCU AUUGAGUGdTdT | 199 | ACUCAAUAGGUAA ACUAUGdTdT | 200 | AL-DP-2099 |
| 5651 | 5649 | AUAGUUUACCUA UUGAGUGUdTdT | 201 | AACUCAAUAGGUA AACUAUdTdT | 202 | AL-DP-2100 |
| 5752 | 5750 | CAUUGGUCUUAU UUACAUAdTdT | 203 | UAUGUAAAUAAGA CCAAUGdTdT | 204 | AL-DP-2101 |
| 5754 | 5752 | UUGGUCUUAUUU ACAUAUAdTdT | 205 | UAUAUGUAAAUAA GACCAAdTdT | 206 | AL-DP-2102 |
| 5755 | 5753 | UGGUCUUAUUUA CAUAUAAdTdT | 207 | UUAUAUGUAAAUA AGACCAdTdT | 208 | AL-DP-2103 |
| 5756 | 5754 | GGUCUUAUUUAC AUAUAAAdTdT | 209 | UUUAUAUGUAAAU AAGACCdTdT | 210 | AL-DP-2141 |
| 5919 | 5917 | AUAUCAUGCUCA AGAUGAUdTdT | 211 | AUCAUCUUGAGCA UGAUAUdTdT | 212 | AL-DP-2142 |
| 5920 | 5918 | UAUCAUGCUCAA GAUGAUAdTdT | 213 | UAUCAUCUUGAGC AUGAUAdTdT | 214 | AL-DP-2104 |
| 5934 | 5932 | UGAUAUUGAUUU CAAAUAGdTdT | 215 | UAAUUUGAAAUCA AUAUCAdTdT | 216 | AL-DP-2105 |
| 6016 | 6014 | UACUUAGUCCUU ACAAUAGdTdT | 217 | CUAUUGUAAGGAC UAAGUAdTdT | 218 | AL-DP-2106 |
| 6019 | 6017 | UUAGUCCUUACA AUAGGUCdTdT | 219 | GACCUAUUGUAAG GACUAAdTdT | 220 | AL-DP-2107 |
| 6020 | 6018 | UAGUCCUUACAA UAGGUCCdTdT | 221 | GGACCUAUUGUAA GGACUAdTdT | 222 | AL-DP-2108 |
| 6252 | 6250 | AUAUUCUAUAGC UGGACGUdTdT | 223 | ACGUCCAGCUAUA GAAUAUdTdT | 224 | AL-DP-2109 |
| 6253 | 6251 | UAUUCUAUAGCU GGACGUAdTdT | 225 | UACGUCCAGCUAU AGAAUAdTdT | 226 | AL-DP-2110 |
| 6254 | 6252 | AUUCUAUAGCUG GACGUAGdTdT | 227 | UUACGUCCAGCUA UAGAAUdTdT | 228 | AL-DP-2111 |

TABLE 1 (a-c)-continued siRNA sequences

Table 1b. RSV P gene

| Actual start | Start_Pos | Sense | SEQ ID NO: | Antisense | SEQ ID NO: | AL-DP # | % inhibition (5 nM) | % inhibition RSV A2 500 pM | % inhibition RSV A2 50 pM | % inhibition RSV A2 5 pM | % inhibition RSV B (5 nM) |
|---|---|---|---|---|---|---|---|---|---|---|---|
| 55 | 53 | AAAUCCUAGAAUCAAUUUdTdT | 229 | UUAUUGAUUCUAGGAAUUUdTdT | 230 | AL-DP-2000 | 3 | | | | |
| 56 | 54 | AAUUCCUAGAAUCAAUAAAdTdT | 231 | UUUAUUGAUUCUAGGAAUUdTdT | 232 | AL-DP-2001 | 4 | | | | |
| 58 | 56 | UUCCUAGAAUCAAUAAAGGdTdT | 233 | CCUUUAUUGAUUCUAGGAAdTdT | 234 | AL-DP-2002 | 7 | | | | |
| 59 | 57 | UCCUAGAAUCAAUAAAGGGdTdT | 235 | CCCUUUAUUGAUUCUAGGAdTdT | 236 | AL-DP-2003 | 98 | 93 | 92 | 84 | 97 |
| 61 | 59 | CUAGAAUCAAUAAAGGGCAdTdT | 237 | UGCCCUUUAUUGAUUCUAGdTdT | 238 | AL-DP-2004 | 3 | | | | |
| 322 | 320 | ACAUUUGAUAACAAUGAAGdTdT | 239 | CUUCAUUGUUAUCAAAUGUdTdT | 240 | AL-DP-2005 | 7 | | | | |
| 323 | 321 | CAUUUGAUAACAAUGAAGAdTdT | 241 | UCUUCAUUGUUAUCAAAUGdTdT | 242 | AL-DP-2006 | 5 | | | | |
| 324 | 322 | AUUUGAUAACAAUGAAAAUdTdT | 243 | UCUUCAUUGUUAUCAAAUdTdT | 244 | AL-DP-2007 | 4 | | | | |
| 325 | 323 | UUUGAUAACAAUGAAGAAGdTdT | 245 | CUUCUUCAUUGUUAUCAAAdTdT | 246 | AL-DP-2008 | 7 | | | | |
| 426 | 424 | AAGUGAAAUACUAGGAAUGdTdT | 247 | CAUUCCUAGUAUUUCACUUdTdT | 248 | AL-DP-2009 | 2 | | | | |
| 427 | 425 | AGUGAAAUACUAGGAAUGCdTdT | 249 | GCAUUCCUAGUAUUUCACUdTdT | 250 | AL-DP-2010 | 7 | | | | |
| 428 | 426 | GUGAAAUACUAGGAAUGCUdTdT | 251 | AGCAUUCCUAGUAUUUCACdTdT | 252 | AL-DP-2011 | 4 | | | | |
| 429 | 427 | UGAAAUACUAGGAAUGCUUdTdT | 253 | AAGCAUUCCUAGUAUUUCAdTdT | 254 | AL-DP-2012 | 96 | 77 | 68 | 66 | 92 |
| 430 | 428 | GAAAUACUAGGAAUGCUUCdTdT | 255 | GAAGCAUUCCUAGUAUUUCdTdT | 256 | AL-DP-2013 | 98 | 85 | 76 | 75 | 89 |
| 431 | 429 | AAAUACUAGGAAUGCUUCAdTdT | 257 | UGAAGCAUUCCUAGUAUUUdTdT | 258 | AL-DP-2014 | 98 | 85 | 81 | 68 | 66 |

TABLE 1 (a-c)-continued siRNA sequences

| Actual start | Sense | SEQ ID NO: | Antisense | SEQ ID NO: | AL-DP # | % inhibition (5 nM) | % inhibition RSV A2 500 pM | % inhibition RSV A2 50 pM | % inhibition RSV A2 5 pM | % inhibition RSV B (5 nM) |
|---|---|---|---|---|---|---|---|---|---|---|
| 550 | GAAGCAUUAAUG ACCAUGAdTdT | 548 | CAUUGGUCAUUAA UGCUUCdTdT | 259 | AL-DP-2015 | 7 | | | | |
| 551 | AAGCAUUAAUGA CCAUGAdTdT | 549 | UCAUUGGUCAUUA AUGCUUdTdT | 261 | AL-DP-2016 | 98 | 88 | 82 | 75 | 94 |
|  | CGAUAAUAUAAC AGCAAGAdTsdT | | UCUUGCUGUUAUA UUAUCGdTsdT | 263 | AL-DP-1729 | 90 | | | | |
|  | CGAUUAUAUUAC AGGAUGAdTsdT | | GCAUUCUGUAAUA UAAUCGdTsdT | 265 | AL-DP-1730 | | | | | |

Table 1c. RSV N gene

| Actual start | Sense | SEQ ID NO: | Antisense | SEQ ID NO: | AL-DP # | % inhibition (5 nM) | % inhibition RSV A2 500 pM | % inhibition RSV A2 50 pM | % inhibition RSV A2 5 pM | % inhibition RSV B (5 nM) |
|---|---|---|---|---|---|---|---|---|---|---|
| 3 | GGCUCUAGCAAA GUCAAGAdTdT | 267 | CUUGACUUUGCU AAGAGCCdTdT | 268 | AL-DP-2017 | 98 | 86 | 84 | 80 | 93 |
| 5 | CUCUUAGCAAAGU CAAGUUdTdT | 269 | AACUUGACUUUG CUAAGAGdTdT | 270 | AL-DP-2018 | 2 | | | | |
| 52 | CUGUCAUCCAGCA AAUACAdTdT | 271 | UGUAUUUGCUGG AUGACAGdTdT | 272 | AL-DP-2019 | 5 | | | | |
| 53 | UGUCAUCCAGCA AUACACAdTdT | 273 | GUGUAUUUGCUG GAUGACAdTdT | 274 | AL-DP-2020 | 2 | | | | |
| 191 | UAAUAGGUAGUU AUAUGCAdTdT | 275 | GCAUAUAACAUA CCUAUUAdTdT | 276 | AL-DP-2021 | 3 | | | | |
| 379 | AUUGAGAUAGAAU CUAGAAdTdT | 277 | UUCUAGAUUCUA UCUCAUdTdT | 278 | AL-DP-2022 | 98 | 78 | 77 | 75 | 94 |
| 897 | AAUUCACCAUAUA UUGAACdTdT | 279 | GUUCAAUAUAUG GUGAAUdTdT | 280 | AL-DP-2023 | 1 | | | | |
| 898 | UUCUACCAUAUAU UGAACAdTdT | 281 | UGUUCAAUAUAU GGUAGAdTdT | 282 | AL-DP-2024 | 7 | | | | |
| 899 | UCUACCAUAUAUU GAACAAdTdT | 283 | UUGUUCAAUAUA UGGUAGAdTdT | 284 | AL-DP-2025 | 96 | 89 | 84 | 77 | 96 |

What is claimed is:

1. An isolated double-stranded ribonucleic acid (dsRNA) for inhibiting the expression of a Respiratory Syncytial virus (RSV) protein, wherein the dsRNA comprises a sense strand and an antisense strand, each strand comprising a 3' end and a 5' end, the antisense strand comprising a region that is complementary to UAGCAUUAAAUAGCCUUAAAUU (SEQ ID NO:285), wherein the sense strand and antisense strand are each 15-30 nucleotides in length and wherein the dsRNA comprises a modification capable of enhancing the stability of the dsRNA in a biological sample.

2. The isolated dsRNA of claim 1, wherein the dsRNA is selected from the group consisting of: AL-DP-2041, AL-DP-2114, AL-DP-2042, and AL-DP-2043.

3. The isolated dsRNA of claim 1, wherein each 3'-end comprises a nucleotide overhang of two nucleotides.

4. The isolated dsRNA of claim 1, wherein the dsRNA is 19-23 nucleotides in length.

5. The isolated dsRNA of claim 1, comprising a phosphorothioate or a 2'-modified nucleotide.

6. The isolated dsRNA of claim 5, wherein the 2'-modified nucleotide comprises a modification selected from the group consisting of: 2'-deoxy, 2'-fluoro, 2'-O-methyl, 2'-O-methoxyethyl (2'-O-MOE), 2'-amino and 2'-aminoalkoxy modified nucleotides.

7. A composition comprising the isolated dsRNA of claim 1 and a ligand, wherein the ligand is tethered to the dsRNA.

8. A method of reducing the levels of a RSV protein, RSV mRNA or RSV titer in lung or respiratory cells in a subject comprising the step of administering an effective amount the dsRNA of claim 1 to the subject wherein administration results in reducing the levels of the RSV protein, RSV mRNA or RSV titer in lung or respiratory cells in the subject.

9. The method of claim 8, wherein the dsRNA is administered intranasally, or by direct administration to the lung of the subject.

10. The method of claim 8, wherein the dsRNA is administered via inhalation or nebulization to the subject.

11. A formulation comprising the dsRNA of claim 1, wherein the formulation comprises at least one pharmaceutical carrier.

12. The formulation of claim 11, further comprising at least one therapeutic agent in addition to the dsRNA.

13. The formulation of claim 12, wherein the at least one therapeutic agent is a second dsRNA.

14. The formulation of claim 11, wherein the formulation comprises a dsRNA stabilizing agent selected from the group comprising a chelator and an RNAse inhibitor.

15. The formulation of claim 11, wherein the at least one pharmaceutical carrier is selected from the group consisting of a polypeptide, an amino acid, a carbohydrate, a surfactant, a phosphate buffered saline (PBS), or another hypertonic saline solution.

16. The formulation of claim 11, wherein the formulation is a respirable particle about 1 to 10 microns in size.

17. A device for generating an aerosol suspension of respirable particles comprising a dsRNA, wherein the device is a nebulizer or a solid particulate therapeutic aerosol generator, and wherein the device comprises a composition comprising the dsRNA of claim 1.

18. The device of claim 17, wherein the device is any one of a pressure driven jet nebulizer, an ultrasonic nebulizer, a solid particulate therapeutic aerosol generator, an insufflator, and a metered dose inhalator.

19. The device of claim 17, wherein the dsRNA comprises up to 40% w/w of the composition.

* * * * *

UNITED STATES PATENT AND TRADEMARK OFFICE
CERTIFICATE OF CORRECTION

| | | |
|---|---|---|
| PATENT NO. | : 8,859,750 B2 | Page 1 of 1 |
| APPLICATION NO. | : 13/434820 | |
| DATED | : October 14, 2014 | |
| INVENTOR(S) | : Rachel Meyers et al. | |

It is certified that error appears in the above-identified patent and that said Letters Patent is hereby corrected as shown below:

On the title page, under abstract "19 Claims, 10 Drawing Sheets" should read --27 Claims, 10 Drawing Sheets--.

In the claims

Column 192, line 55, after claim 19, insert

--20. The isolated dsRNA of claim 1, wherein the dsRNA consists of AL-DP-2041.
21. The isolated dsRNA of claim 1, wherein the dsRNA consists of AL-DP-2114.
22. The isolated dsRNA of claim 1, wherein the dsRNA consists of AL-DP-2042.
23. The isolated dsRNA of claim 1, wherein the dsRNA consists of AL-DP-2043.
24. A composition comprising the isolated dsRNA of claim 20, 21, 22, or 23 and a ligand, wherein the ligand is tethered to the dsRNA.
25. A method of reducing the levels of a RSV protein, RSV mRNA or RSV titer in lung or respiratory cells in a subject comprising the step of administering an effective amount the dsRNA of claim 20, 21, 22, or 23 to the subject wherein administration results in reducing the levels of the RSV protein, RSV mRNA or RSV titer in lung or respiratory cells in the subject.
26. A formulation comprising the dsRNA of claim 20, 21, 22, or 23, wherein the formulation comprises at least one pharmaceutical carrier.
27. A device for generating an aerosol suspension of respirable particles comprising a dsRNA, wherein the device is a nebulizer or a solid particulate therapeutic aerosol generator, and wherein the device comprises a composition comprising the dsRNA of claim 20, 21, 22, or 23.--

Signed and Sealed this
Twenty-fourth Day of May, 2016

Michelle K. Lee
*Director of the United States Patent and Trademark Office*

SEQUENCE LISTING

<160> NUMBER OF SEQ ID NOS: 285

<210> SEQ ID NO 1
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 1
ggaucccauu auuaauggat t                                             21

<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 2
uccauuaaua augggauccu t                                             21

<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 3 gauccauua uuaauggaat t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 4
uuccauuaau aaugggauct t                                              21

```
<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 5
```
aguuauuuaa aagguguuat t                                              21

```
<210> SEQ ID NO 6
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 6
```
uaacaccuuu uaaauaacut t                                              21

```
<210> SEQ ID NO 7
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 7
```
guuauuuaaa agguguuaut t                                              21

```
<210> SEQ ID NO 8
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine
```

```
<400> SEQUENCE: 8
auaacaccuu uuaaauaact t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 9
auuuaaaagg uguuaucuct t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 10
gagauaacac cuuuuaaaut t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 11
uuaaaaggug uuaucucuut t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine
```

```
<400> SEQUENCE: 12
aagagauaac accuuuuaat t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 13
aaguccacua cuagagcaut t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 14
augcucuagu aguggacuut t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 15
aguccacuac uagagcauat t                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
```

```
<223> OTHER INFORMATION: Deoxythymidine

<400> SEQUENCE: 16
uaugcucuag uaguggacut t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 17
guccacuacu agagcauaut t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 18
auaugcucua guaguggact t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 19
uccacuacua gagcauaugt t                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
```

<222> LOCATION: (20)..(21)
<223> OTHER INFORMATION: Deoxythymidine

<400> SEQUENCE: 20
cauaugcucu aguaguggat t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 21
gaagagcuau agaaauaagt t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 22
cuuauuucua uagcucuuct t                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 23
gagcuauaga aauaagugat t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:

<221> NAME/KEY: modified_base
<222> LOCATION: (20)..(21)
<223> OTHER INFORMATION: Deoxythymidine

<400> SEQUENCE: 24
ucacuuauuu cuauagcuct t					21

<210> SEQ ID NO 25
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 25
cuauagaaau aagugaugut t					21

<210> SEQ ID NO 26
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 26
acaucacuua uuucuauagt t					21

<210> SEQ ID NO 27
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 27
ucaaaacaac acucuugaat t					21

<210> SEQ ID NO 28
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (20)..(21)
<223> OTHER INFORMATION: Deoxythymidine

<400> SEQUENCE: 28
uucaagagug uuguuuugat t                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 29
uagagggauu uauuauguct t                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 30
gacauaauaa aucccucuat t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 31
auaaaagggu uuguaaauat t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
``` oligonucleotide
<220> FEATURE:
<221> NAME/KEY: modified_base
<222> LOCATION: (20)..(21)
<223> OTHER INFORMATION: Deoxythymidine

<400> SEQUENCE: 32
uauuuacaaa cccuuuuaut t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 33
cucaguguag guagaauggut t                                             21

<210> SEQ ID NO 34
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 34
acauucuacc uacacugagt t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 35
ucaguguagg uagaauguut t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 36
aacauucuac cuacacugat t                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 37
caguguaggu agaauguuut t                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 38
aaacauucua ccuacacugt t                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 39
aguguaggua gaauguuugt t                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 40
caaacauucu accuacacut t                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 41
guguagguag aauguuugct t                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 42
gcaaacauuc uaccuacact t                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 43
acaagauaug gugaucuagt t                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Combined DNA/RNA Molecule:
```

-continued

Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 44
cuagaucacc auaucuugut t                                                 21

<210> SEQ ID NO 45
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 45
agcaaauuca aucaagcaut t                                                 21

<210> SEQ ID NO 46
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 46
augcuugauu gaauuugcut t                                                 21

<210> SEQ ID NO 47
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 47
gcaaauucaa ucaagcauut t                                                 21

<210> SEQ ID NO 48
<211> LENGTH: 21
<212> TYPE: DNA
<213> ORGANISM: Artificial Sequence
<220> FEATURE:

<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 48
aaugcuugau ugaauuugct t                                               21

<210> SEQ ID NO 49
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 49
gaugaacaaa guggauuaut t                                               21

<210> SEQ ID NO 50
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 50
auaauccacu uuguucauct t                                               21

<210> SEQ ID NO 51
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 51
uaauaucucu caaagggaat t                                               21

<210> SEQ ID NO 52
<211> LENGTH: 21
<212> TYPE: DNA
<213> ORGANISM: Artificial Sequence

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 52
uucccuuuga gagauauuat t                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 53
auaucucuca aagggaaaut t                                              21

<210> SEQ ID NO 54
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 54
auuucccuuu gagagauaut t                                              21

<210> SEQ ID NO 55
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 55
uaucucucaa agggaaauut t                                              21

<210> SEQ ID NO 56
<211> LENGTH: 21
<212> TYPE: DNA
```

```
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 56
aauuucccuu ugagagauat t                                                  21

<210> SEQ ID NO 57
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 57
caugcucaag cagauuauut t                                                  21

<210> SEQ ID NO 58
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 58
aauaaucugc uugagcaugt t                                                  21

<210> SEQ ID NO 59
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 59
ugcucaagca gauuauuugt t                                                  21

<210> SEQ ID NO 60
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 60
caaauaaucu gcuugagcat t                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 61
uagcauuaaa uagccuuaat t                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 62
uuaaggcuau uuaaugcuat t                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 63
agcauuaaau agccuuaaat t                                              21

<210> SEQ ID NO 64
```

```
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 64
uuuaaggcua uuuaaugcut t                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 65
gcauuaaaua gccuuaaaut t                                              21

<210> SEQ ID NO 66
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 66
auuuaaggcu auuuaaugct t                                              21

<210> SEQ ID NO 67
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 67
cauuaaauag ccuuaaauut t                                              21
```

```
<210> SEQ ID NO 68
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 68
aauuuaaggc uauuuaaugt t                                              21

<210> SEQ ID NO 69
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 69
uauuaugcag uuuaauauut t                                              21

<210> SEQ ID NO 70
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 70
aauauuaaac ugcauaaauat t                                             21

<210> SEQ ID NO 71
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 71
uuaugcaguu uaauauuuat t                                              21
```

```
<210> SEQ ID NO 72
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 72
uaaauauuaa acugcauaat t                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 73
aaaagugcac aacauuauat t                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 74
uauaauguug ugcacuuuut t                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 75
aaagugcaca acauuauact t                                              21
```

<210> SEQ ID NO 76
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 76
guauaauguu gugcacuuut t                                           21

<210> SEQ ID NO 77
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 77
auauagaacc uacauaucct t                                           21

<210> SEQ ID NO 78
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 78
ggauauguag guucuauaut t                                           21

<210> SEQ ID NO 79
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 79
uauagaaccu acauauccut t         21

<210> SEQ ID NO 80
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 80
aggauaugua gguucuauat t         21

<210> SEQ ID NO 81
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 81
uaagaguugu uuaugaaagt t         21

<210> SEQ ID NO 82
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 82
cuuucauaaa caacucuuat t         21

<210> SEQ ID NO 83
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 83
acagucagua guagaccaut t                                              21

<210> SEQ ID NO 84
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 84 auggcuacu acugacugut t                                               21

<210> SEQ ID NO 85
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 85
cagucaguag uagaccaugt t                                              21

<210> SEQ ID NO 86
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 86 cauggcuac uacugacugt t                                               21

<210> SEQ ID NO 87
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

```
<400> SEQUENCE: 87
agucaguagu agaccaugut t                                              21

<210> SEQ ID NO 88
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 88
acauggucua cuacugacut t                                              21

<210> SEQ ID NO 89
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 89
gucaguagua gaccaugugt t                                              21

<210> SEQ ID NO 90
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 90
cacauggucu acuacugact t                                              21

<210> SEQ ID NO 91
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine
```

<400> SEQUENCE: 91
ucaguaguag accaugugat t                                              21

<210> SEQ ID NO 92
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 92
ucacaugguc uacuacugat t                                              21

<210> SEQ ID NO 93
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 93
caugugaauu cccugcauct t                                              21

<210> SEQ ID NO 94
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 94
gaugcaggga auucacaugt t                                              21

<210> SEQ ID NO 95
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)

<223> OTHER INFORMATION: Deoxythymidine

<400> SEQUENCE: 95
augugaauuc ccugcaucat t                                              21

<210> SEQ ID NO 96
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 96
ugaugcaggg aauucacaut t                                              21

<210> SEQ ID NO 97
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 97
ugugaauucc cugcaucaat t                                              21

<210> SEQ ID NO 98
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 98
uugaugcagg gaauucacat t                                              21

<210> SEQ ID NO 99
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 99
gugaauuccc ugcaucaaut t                                              21

<210> SEQ ID NO 100
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 100
auugaugcag ggaauucact t                                              21

<210> SEQ ID NO 101
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 101
aauucccugc aucaauacct t                                              21

<210> SEQ ID NO 102
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 102
gguauugaug cagggaauut t                                              21

<210> SEQ ID NO 103
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (20)..(21)
<223> OTHER INFORMATION: Deoxythymidine

<400> SEQUENCE: 103
gcaucaauac cagcuuauat t                                              21

<210> SEQ ID NO 104
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 104
uauaagcugg uauugaugct t                                              21

<210> SEQ ID NO 105
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 105
caucaauacc agcuuauagt t                                              21

<210> SEQ ID NO 106
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 106
cuauaagcug guauugaugt t                                              21

<210> SEQ ID NO 107
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

-continued

```
<220> FEATURE:
<221> NAME/KEY: modified_base
<222> LOCATION: (20)..(21)
<223> OTHER INFORMATION: Deoxythymidine

<400> SEQUENCE: 107
auaccagcuu auagaacaat t                                                  21

<210> SEQ ID NO 108
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 108
uuguucuaua agcugguaut t                                                  21

<210> SEQ ID NO 109
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 109
uaccagcuua uagaacaact t                                                  21

<210> SEQ ID NO 110
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 110
guuguucuau aagcugguat t                                                  21

<210> SEQ ID NO 111
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
``` oligonucleotide
<220> FEATURE:
<221> NAME/KEY: modified_base
<222> LOCATION: (20)..(21)
<223> OTHER INFORMATION: Deoxythymidine

<400> SEQUENCE: 111
accagcuuau agaacaacat t                                              21

<210> SEQ ID NO 112
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 112
uguuguucua uaagcuggut t                                              21

<210> SEQ ID NO 113
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 113
ccagcuuaua gaacaacaat t                                              21

<210> SEQ ID NO 114
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 114
uuguuguucu auaagcuggt t                                              21

<210> SEQ ID NO 115
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:

-continued

```
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 115
cagcuuauag aacaacaaat t                                           21

<210> SEQ ID NO 116
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 116
uuuguuguuc uauaagcugt t                                           21

<210> SEQ ID NO 117
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 117
auagaacaac aaauuaucat t                                           21

<210> SEQ ID NO 118
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 118
ugauaauuug uuguucuaut t                                           21

<210> SEQ ID NO 119
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 119
uauuaacaga aaaguauggt t                                                    21

<210> SEQ ID NO 120
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 120
ccauacuuuu cuguuaauat t                                                    21

<210> SEQ ID NO 121
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 121
ugagauacau uugaugaaat t                                                    21

<210> SEQ ID NO 122
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 122
uuucaucaaa uguaucucat t                                                    21

<210> SEQ ID NO 123
<211> LENGTH: 21
<212> TYPE: DNA
<213> ORGANISM: Artificial Sequence
<220> FEATURE:
<223> OTHER INFORMATION: Description of Combined DNA/RNA Molecule:
```

```
              Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 123
gagauacauu ugaugaaact t                                              21

<210> SEQ ID NO 124
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 124
guuucaucaa auguaucct t                                               21

<210> SEQ ID NO 125
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 125
gauacauuug augaaaccut t                                              21

<210> SEQ ID NO 126
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 126
agguuucauc aaauguauct t                                              21

<210> SEQ ID NO 127
<211> LENGTH: 21
<212> TYPE: DNA
<213> ORGANISM: Artificial Sequence
<220> FEATURE:
```

<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 127
auacauuuga ugaaaccuct t                                              21

<210> SEQ ID NO 128
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 128
gagguuucau caaauguaut t                                              21

<210> SEQ ID NO 129
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 129
uacauuugau gaaaccucct t                                              21

<210> SEQ ID NO 130
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 130
ggagguuuca ucaaauguat t                                              21

<210> SEQ ID NO 131
<211> LENGTH: 21
<212> TYPE: DNA
<213> ORGANISM: Artificial Sequence

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 131
aagugauaca aaaacagcat t                                            21

<210> SEQ ID NO 132
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 132
ugcuguuuuu guaucacuut t                                            21

<210> SEQ ID NO 133
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 133
agugauacaa aaacagcaut t                                            21

<210> SEQ ID NO 134
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 134
augcuguuuu uguaucacut t                                            21

<210> SEQ ID NO 135
<211> LENGTH: 21
<212> TYPE: DNA
```

```
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 135
ugauacaaaa acagcauaut t                                                21

<210> SEQ ID NO 136
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 136
auaugcuguu uuuguaucat t                                                21

<210> SEQ ID NO 137
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 137
uuuaaguacu aauuuagcut t                                                21

<210> SEQ ID NO 138
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 138
agcuaaauua guacuuaaat t                                                21

<210> SEQ ID NO 139
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 139
uuaaguacua auuuagcugt t                                              21

<210> SEQ ID NO 140
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 140
cagcuaaauu aguacuuaat t                                              21

<210> SEQ ID NO 141
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 141
uaaguacuaa uuuagcuggt t                                              21

<210> SEQ ID NO 142
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 142
ccagcuaaau uaguacuuat t                                              21

<210> SEQ ID NO 143
```

```
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 143
aaguacuaau uuagcuggat t                                              21

<210> SEQ ID NO 144
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 144
uccagcuaaa uuaguacuut t                                              21

<210> SEQ ID NO 145
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 145
aguacuaauu uagcuggact t                                              21

<210> SEQ ID NO 146
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 146
guccagcuaa auuaguacut t                                              21
```

```
<210> SEQ ID NO 147
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 147
guacuaauuu agcuggacat t                                              21

<210> SEQ ID NO 148
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 148
uguccagcua aauuaguact t                                              21

<210> SEQ ID NO 149
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 149
acuaauuuag cuggacauut t                                              21

<210> SEQ ID NO 150
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 150
aauguccagc uaaauuagut t                                              21
```

```
<210> SEQ ID NO 151
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 151
aauuuagcug gacauuggat t                                            21

<210> SEQ ID NO 152
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 152
uccaaugucc agcuaaaauu t                                            21

<210> SEQ ID NO 153
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 153
auuuagcugg acauuggaut t                                            21

<210> SEQ ID NO 154
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 154
auccaauguc cagcuaaaut t                                            21
```

<210> SEQ ID NO 155
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 155
uuagcuggac auuggauuct t                                                  21

<210> SEQ ID NO 156
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 156
gaauccaaug uccagcuaat t                                                  21

<210> SEQ ID NO 157
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 157
uuuugaaaaa gauuggggat t                                                  21

<210> SEQ ID NO 158
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 158

-continued uccccaaucu uuuucaaaat t                                     21

<210> SEQ ID NO 159
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 159
uuugaaaaag auugggagt t                                      21

<210> SEQ ID NO 160
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 160
cuccccaauc uuuuucaaat t                                     21

<210> SEQ ID NO 161
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 161
ugaaaaagau uggggagagt t                                     21

<210> SEQ ID NO 162
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 162 cucucccaa ucuuuuucat t                                              21

<210> SEQ ID NO 163
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 163
gaaaaagauu ggggagaggt t                                             21

<210> SEQ ID NO 164
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 164
ccucucccca aucuuuuuct t                                             21

<210> SEQ ID NO 165
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 165
uaugaacacu ucagaucuut t                                             21

<210> SEQ ID NO 166
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

```
<400> SEQUENCE: 166
aagaucugaa guguucauat t                                              21

<210> SEQ ID NO 167
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 167
augaacacuu cagaucuuct t                                              21

<210> SEQ ID NO 168
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 168
gaagaucuga aguguucaut t                                              21

<210> SEQ ID NO 169
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 169
ugcccuuggg uuguuaacat t                                              21

<210> SEQ ID NO 170
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine
```

<400> SEQUENCE: 170
uguuaacaac ccaagggcat t                                              21

<210> SEQ ID NO 171
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 171
gcccuugggu uguuaacaut t                                              21

<210> SEQ ID NO 172
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 172
auguuaacaa cccaagggct t                                              21

<210> SEQ ID NO 173
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 173
uauagcauuc auaggugaat t                                              21

<210> SEQ ID NO 174
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)

<223> OTHER INFORMATION: Deoxythymidine

<400> SEQUENCE: 174
uucaccuaug aaugcuauat t                                      21

<210> SEQ ID NO 175
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 175
auagcauuca uaggugaagt t                                      21

<210> SEQ ID NO 176
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 176
cuucaccuau gaaugcuaut t                                      21

<210> SEQ ID NO 177
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 177
uagcauucau aggugaaggt t                                      21

<210> SEQ ID NO 178
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (20)..(21)
<223> OTHER INFORMATION: Deoxythymidine

<400> SEQUENCE: 178
ccuucaccua ugaaugcuat t                                              21

<210> SEQ ID NO 179
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 179
auucauaggu gaaggagcat t                                              21

<210> SEQ ID NO 180
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 180
ugcuccuuca ccuaugaaut t                                              21

<210> SEQ ID NO 181
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 181
uugcaaugau cauaguuuat t                                              21

<210> SEQ ID NO 182
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
```

<221> NAME/KEY: modified_base
<222> LOCATION: (20)..(21)
<223> OTHER INFORMATION: Deoxythymidine

<400> SEQUENCE: 182
uaaacuauga ucauugcaat t                                              21

<210> SEQ ID NO 183
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 183
ugcaaugauc auaguuuact t                                              21

<210> SEQ ID NO 184
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 184
guaaacuaug aucauugcat t                                              21

<210> SEQ ID NO 185
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 185
gcaaugauca uaguuuacct t                                              21

<210> SEQ ID NO 186
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (20)..(21)
<223> OTHER INFORMATION: Deoxythymidine

<400> SEQUENCE: 186
gguaaacuau gaucauugct t                                              21

<210> SEQ ID NO 187
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 187
caaugaucau aguuuaccut t                                              21

<210> SEQ ID NO 188
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 188
agguaaacua ugaucauugt t                                              21

<210> SEQ ID NO 189
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 189
aaugaucaua guuuaccuat t                                              21

<210> SEQ ID NO 190
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
```

```
        oligonucleotide
<220> FEATURE:
<221> NAME/KEY: modified_base
<222> LOCATION: (20)..(21)
<223> OTHER INFORMATION: Deoxythymidine

<400> SEQUENCE: 190
uagguaaacu augaucauut t                                            21

<210> SEQ ID NO 191
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 191
augaucauag uuuaccuaut t                                            21

<210> SEQ ID NO 192
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 192
auagguaaac uaugaucaut t                                            21

<210> SEQ ID NO 193
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 193
gaucauaguu uaccuauugt t                                            21

<210> SEQ ID NO 194
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 194
caauagguaa acuaugauct t                                              21

<210> SEQ ID NO 195
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 195
aucauaguuu accuauugat t                                              21

<210> SEQ ID NO 196
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 196
ucaauaggua aacuaugaut t                                              21

<210> SEQ ID NO 197
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 197
ucauaguuua ccuauugagt t                                              21

<210> SEQ ID NO 198
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 198
cucaauaggu aaacuaugat t                                              21

<210> SEQ ID NO 199
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 199
cauaguuuac cuauugagut t                                              21

<210> SEQ ID NO 200
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 200
acucaauagg uaaacuaugt t                                              21

<210> SEQ ID NO 201
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 201
auaguuuacc uauugaguut t                                              21

<210> SEQ ID NO 202
<211> LENGTH: 21
<212> TYPE: DNA
<213> ORGANISM: Artificial Sequence
<220> FEATURE:
<223> OTHER INFORMATION: Description of Combined DNA/RNA Molecule:
```

Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 202
aacucaauag guaaacuaut t                                              21

<210> SEQ ID NO 203
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 203
cauuggucuu auuuacauat t                                              21

<210> SEQ ID NO 204
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 204
uauguaaaua agaccaaugt t                                              21

<210> SEQ ID NO 205
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 205
uuggucuuau uuacauauat t                                              21

<210> SEQ ID NO 206
<211> LENGTH: 21
<212> TYPE: DNA
<213> ORGANISM: Artificial Sequence
<220> FEATURE:

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 206
uauauguaaa uaagaccaat t                                                   21

<210> SEQ ID NO 207
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 207
uggucuuauu uacauauaat t                                                   21

<210> SEQ ID NO 208
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 208
uuauauguaa auaagaccat t                                                   21

<210> SEQ ID NO 209
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 209
ggucuuauuu acauauaaat t                                                   21

<210> SEQ ID NO 210
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 210
uuuauaugua aauaagacct t                                              21

<210> SEQ ID NO 211
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 211
auaucaugcu caagaugaut t                                              21

<210> SEQ ID NO 212
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 212
aucaucuuga gcaugauaut t                                              21

<210> SEQ ID NO 213
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 213
uaucaugcuc aagaugauat t                                              21

<210> SEQ ID NO 214
<211> LENGTH: 21
<212> TYPE: DNA
```

```
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 214
uaucaucuug agcaugauat t                                             21

<210> SEQ ID NO 215
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 215
ugauauugau uucaaauuat t                                             21

<210> SEQ ID NO 216
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 216
uaauuugaaa ucaauaucat t                                             21

<210> SEQ ID NO 217
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 217
uacuuagucc uuacaauagt t                                             21

<210> SEQ ID NO 218
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 218
cuauuguaag gacuaaguat t                                              21

<210> SEQ ID NO 219
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 219
uuaguccuua caauagguct t                                              21

<210> SEQ ID NO 220
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 220
gaccuauugu aaggacuaat t                                              21

<210> SEQ ID NO 221
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 221
uaguccuuac aauagguect t                                              21

<210> SEQ ID NO 222
```

-continued

```
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 222
ggaccuauug uaaggacuat t                                              21

<210> SEQ ID NO 223
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 223
auauucuaua gcuggacgut t                                              21

<210> SEQ ID NO 224
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 224
acguccagcu auagaauaut t                                              21

<210> SEQ ID NO 225
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 225
uauucuauag cuggacguat t                                              21
```

```
<210> SEQ ID NO 226
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 226
uacguccagc uauagaauat t                                              21

<210> SEQ ID NO 227
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 227
auucuauagc uggacguaat t                                              21

<210> SEQ ID NO 228
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 228
uuacguccag cuauagaaut t                                              21

<210> SEQ ID NO 229
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 229
aaauuccuag aaucaauaat t                                              21
```

```
<210> SEQ ID NO 230
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 230
uuauugauuc uaggaauuut t                                             21

<210> SEQ ID NO 231
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 231
aauuccuaga aucaauaaat t                                             21

<210> SEQ ID NO 232
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 232
uuuauugauu cuaggaauut t                                             21

<210> SEQ ID NO 233
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 233
uuccuagaau caauaaaggt t                                             21
```

```
<210> SEQ ID NO 234
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 234
ccuuuauuga uucuaggaat t                                                    21

<210> SEQ ID NO 235
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 235
uccuagaauc aauaaagggt t                                                    21

<210> SEQ ID NO 236
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 236
cccuuuauug auucuaggat t                                                    21

<210> SEQ ID NO 237
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 237
```
cuagaaucaa uaaagggcat t                                              21

<210> SEQ ID NO 238
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 238
ugcccuuuau ugauucuagt t                                              21

<210> SEQ ID NO 239
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 239
acauuugaua acaaugaagt t                                              21

<210> SEQ ID NO 240
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 240
cuucauuguu aucaaaugut t                                              21

<210> SEQ ID NO 241
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 241
cauuugauaa caaugaagat t                                              21

<210> SEQ ID NO 242
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 242
ucuucauugu uaucaaaugt t                                              21

<210> SEQ ID NO 243
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 243
auuugauaac aaugaagaat t                                              21

<210> SEQ ID NO 244
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 244
uucuucauug uuaucaaaut t                                              21

<210> SEQ ID NO 245
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

```
<400> SEQUENCE: 245
uuugauaaca augaagaagt t                                              21

<210> SEQ ID NO 246
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 246
cuucuucauu guuaucaaat t                                              21

<210> SEQ ID NO 247
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 247
aagugaaaua cuaggaaugt t                                              21

<210> SEQ ID NO 248
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 248
cauuccuagu auuucacuut t                                              21

<210> SEQ ID NO 249
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine
```

<400> SEQUENCE: 249
agugaaauac uaggaaugct t                                          21

<210> SEQ ID NO 250
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 250 gcauccuag uauuucacut t                                           21

<210> SEQ ID NO 251
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 251
gugaaauacu aggaaugcut t                                          21

<210> SEQ ID NO 252
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 252 agcauccua guauuucact t                                           21

<210> SEQ ID NO 253
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)

<223> OTHER INFORMATION: Deoxythymidine

<400> SEQUENCE: 253
ugaaauacua ggaaugcuut t                                              21

<210> SEQ ID NO 254
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 254
aagcauuccu aguauuucat t                                              21

<210> SEQ ID NO 255
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 255
gaaauacuag gaaugcuuct t                                              21

<210> SEQ ID NO 256
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 256
gaagcauucc uaguauuuct t                                              21

<210> SEQ ID NO 257
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (20)..(21)
<223> OTHER INFORMATION: Deoxythymidine

<400> SEQUENCE: 257
aaauacuagg aaugcuucat t                                              21

<210> SEQ ID NO 258
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 258
ugaagcauuc cuaguauuut t                                              21

<210> SEQ ID NO 259
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 259
gaagcauuaa ugaccaaugt t                                              21

<210> SEQ ID NO 260
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 260
cauuggucau uaaugcuuct t                                              21

<210> SEQ ID NO 261
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (20)..(21)
<223> OTHER INFORMATION: Deoxythymidine

<400> SEQUENCE: 261
aagcauuaau gaccaaugat t                                              21

<210> SEQ ID NO 262
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 262
ucauugguca uuaaugcuut t                                              21

<210> SEQ ID NO 263
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Deoxythymidine phosphorothioate linkage
<220> FEATURE:
<221> NAME/KEY: modified_base
<222> LOCATION: (21)..(21)
<223> OTHER INFORMATION: Deoxythymidine

<400> SEQUENCE: 263
cgauaauaua acagcaagat t                                              21

<210> SEQ ID NO 264
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Deoxythymidine phosphorothioate linkage
<220> FEATURE:
<221> NAME/KEY: modified_base
<222> LOCATION: (21)..(21)
<223> OTHER INFORMATION: Deoxythymidine

<400> SEQUENCE: 264
ucuugcuguu auauuaucgt t                                              21

<210> SEQ ID NO 265
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Deoxythymidine phosphorothioate linkage
<220> FEATURE:
<221> NAME/KEY: modified_base
<222> LOCATION: (21)..(21)
<223> OTHER INFORMATION: Deoxythymidine

<400> SEQUENCE: 265
cgauuauauu acaggaugat t                                              21

<210> SEQ ID NO 266
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Deoxythymidine phosphorothioate linkage
<220> FEATURE:
<221> NAME/KEY: modified_base
<222> LOCATION: (21)..(21)
<223> OTHER INFORMATION: Deoxythymidine

<400> SEQUENCE: 266
ucauccugua auauaaucgt t                                              21

<210> SEQ ID NO 267
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 267
ggcucuuagc aaagucaagt t                                              21

<210> SEQ ID NO 268
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
```

<223> OTHER INFORMATION: Deoxythymidine

<400> SEQUENCE: 268
cuugacuuug cuaagagcct t                                              21

<210> SEQ ID NO 269
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 269
cucuuagcaa agucaaguut t                                              21

<210> SEQ ID NO 270
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 270
aacuugacuu ugcuaagagt t                                              21

<210> SEQ ID NO 271
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 271
cugucaucca gcaaauacat t                                              21

<210> SEQ ID NO 272
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (20)..(21)
<223> OTHER INFORMATION: Deoxythymidine

<400> SEQUENCE: 272
uguauuugcu ggaugacagt t                                              21

<210> SEQ ID NO 273
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 273
ugucauccag caaauacact t                                              21

<210> SEQ ID NO 274
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 274
guguauuugc uggaugacat t                                              21

<210> SEQ ID NO 275
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 275
uaauagguau guuauaugct t                                              21

<210> SEQ ID NO 276
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
```

<221> NAME/KEY: modified_base
<222> LOCATION: (20)..(21)
<223> OTHER INFORMATION: Deoxythymidine

<400> SEQUENCE: 276
gcauauaaca uaccuauuat t                                              21

<210> SEQ ID NO 277
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 277
auugagauag aaucuagaat t                                              21

<210> SEQ ID NO 278
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 278
uucuagauuc uaucucaaut t                                              21

<210> SEQ ID NO 279
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 279
auucuaccau auauugaact t                                              21

<210> SEQ ID NO 280
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (20)..(21)
<223> OTHER INFORMATION: Deoxythymidine

<400> SEQUENCE: 280
guucaauaua ugguagaaut t                                              21

<210> SEQ ID NO 281
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 281
uucuaccaua uauugaacat t                                              21

<210> SEQ ID NO 282
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 282
uguucaauau augguagaat t                                              21

<210> SEQ ID NO 283
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: Deoxythymidine

<400> SEQUENCE: 283
ucuaccauau auugaacaat t                                              21

<210> SEQ ID NO 284
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
```

```
            oligonucleotide
<220> FEATURE:
<221> NAME/KEY: modified_base
<222> LOCATION: (20)..(21)
<223> OTHER INFORMATION: Deoxythymidine

<400> SEQUENCE: 284
uuguucaaua uauggaugat t                                        21

<210> SEQ ID NO 285
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
uagcauuaaa uagccuuaaa uu                                       22
```